US008554490B2

(12) United States Patent
Tang et al.

(10) Patent No.: US 8,554,490 B2
(45) Date of Patent: Oct. 8, 2013

(54) AUTOMATIC VASCULAR MODEL GENERATION BASED ON FLUID-STRUCTURE INTERACTIONS (FSI)

(75) Inventors: Dalin Tang, Shrewsbury, MA (US); Zhongzhao Teng, Lianjiang (CN)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

(21) Appl. No.: 13/201,946

(22) PCT Filed: Feb. 18, 2010

(86) PCT No.: PCT/US2010/024527
§ 371 (c)(1),
(2), (4) Date: Aug. 17, 2011

(87) PCT Pub. No.: WO2010/099016
PCT Pub. Date: Sep. 2, 2010

(65) Prior Publication Data
US 2011/0295579 A1      Dec. 1, 2011

Related U.S. Application Data

(60) Provisional application No. 61/208,501, filed on Feb. 25, 2009.

(51) Int. Cl.
*G06F 19/00* (2011.01)
*G06K 9/00* (2006.01)
*G06K 9/20* (2006.01)
*G06K 9/36* (2006.01)
*A61B 5/02* (2006.01)

(52) U.S. Cl.
USPC ............. 702/19; 600/481; 600/508; 382/128; 382/282; 382/286

(58) Field of Classification Search
None
See application file for complete search history.

(56) References Cited

U.S. PATENT DOCUMENTS

| 7,751,984 | B2 | 7/2010 | Tang |
| 2004/0153128 | A1 | 8/2004 | Suresh et al. |
| 2005/0187461 | A1 | 8/2005 | Murphy et al. |
| 2006/0149522 | A1 | 7/2006 | Tang |
| 2008/0228086 | A1 | 9/2008 | Ilegbusi et al. |
| 2008/0319308 | A1 | 12/2008 | Tang |

FOREIGN PATENT DOCUMENTS

WO    WO 2006/062958 A2    6/2006

OTHER PUBLICATIONS

Adina Release Notes 8.2, Jan. 2005.*
Huang, X.. et al., "Patient-Specific Artery Shrinkage and 3D Zero-Stress State in Multi-Component 3D FSI Models for Carotid Atherosclerotic Plaques Based on In Vivo MRI Data", *Mol. Cell. Biomech.*, 6(2): 121-134 (2009).
International Search Report and Written Opinion of the International Searching Authority dated Apr. 29, 2010 from International Publication No. PCT/US2010/024527 filed Feb. 18, 2010.
Tang, D. et al., "3D MRI-Based Anisotropic FSI Models with Cyclic Bending for Human Coronary Atherosclerotic Plaque Mechanical Analysis", *J. Biomech. Eng.*, 131(6): (Jun. 2009).
Tang, D. et al., "Effect of Stenosis Asymmetry on Blood Flow and Artery Compression: A Three-Dimensional Fluid-Structure Interaction Model", *Ann. Biomed. Eng.*, 31: 1182-1193 (2003).
Tang, D. et al., "Mechanical Image Analysis Using Finite Element Method, Carotid Disease: The Role of Imaging in Diagnosis and Management", *C.Cambridge University Press*, pp. 324-340 (2006).
Tang, D. et al., "Quantifying Effects of Plaque Structure and Material Properties on Stress Behaviors in Human Atherosclerotic Plaques Using 3D FSI Models", *J. Biomech. Eng.*, 127(7): 1185-1194 (2005).
Tang, D., "Flow in Healthy and Stenosed Arteries", *Wiley Encyclopedia of Biomedical Engineering*, Article 1525 (NJ: John Wiley & Sons, Inc.), pp. 1-14 (2006).
Tang, D., et al., "3D MRI-Based Multicomponent FSI Models for Atherosclerotic", *Ann. Biomed. Eng.*, 32(7), pp. 947-960 (Jul. 2004).
Tang, D., et al., "Effects of a Lipid Pool on Stress/Strain Distributions in Stenotic Arteries: 3D Fluid-Structure Interactions (FSI) Models", *J. Biomech. Eng.*, 126: 363-370 (2004).
Tang, D., et al., "Local Maximal Stress Hypothesis and Computational Plaque Vulnerability Index for Atherosclerotic Plaque Assessment", *Ann. Biomed. Eng.*, 33(12): 1789-1801 (Dec. 2005).
Yang, C., et al., "In Vivo/Ex Vivo MRI-Based 3D Non-Newtonian FSI Models for Human Atherosclerotic Plaques Compared with Fluid/Wall-Only Models", *Comput. Model. Eng. Sci.*, 19(3): 233-245 (2007).
Tang, D., et al., "A Viscoelastic Model and Meshless GFD Method for Blood Flow in Collapsible Stenotic Arteries", Advances in Computational Engineering & Sciences, Chap. 11, International Conference on Computational Engineering and Sciences, Norcross, GA Tech Science Press (2002).
International Preliminary Report on Patentability issued Aug. 30, 2011 from International Application No. PCT/US2010/024527 filed on Feb. 18, 2010.
Lee, K.W. et aL., "Ultrasound image-based computer model of a common carotid artery with a plaque," *Medical Engineering & Physics* 26(823-840), 2004.

(Continued)

*Primary Examiner* — Lori A Clow
(74) *Attorney, Agent, or Firm* — Hamilton, Brook, Smith & Reynolds, P.C.

(57) ABSTRACT

A computer system and method are disclosed for automatically generating a vascular model of a blood vessel to support, for example, identification of mechanical factors corresponding to the blood vessel. The method includes interpolating data points corresponding to a contour of the blood vessel; generating a structural model representing three-dimensional structural characteristics of the blood vessel based on interpolated contours; generating a fluid model representing three-dimensional characteristics of fluid flow within the vessel; and generating a vascular model based on the structural model and the fluid model. The method may also include performing a mechanical analysis of the vascular model to identify a mechanical factor associated with the vessel, for example, a factor associated with a potential plaque rupture within the vessel. Embodiments of the invention are applicable to the diagnosis, assessment, or treatment of cardiovascular diseases.

30 Claims, 23 Drawing Sheets

(56) References Cited

OTHER PUBLICATIONS

Gerbeau, Jean-Frederic, et al., "Fluid-Structure Interaction in Blood Flows on Geometries coming from Medical Imaging," *Rapports de Recherche No. 5052*, Dec. 2003 (retrieved from the Internet: URL: http://www.ann.jussieu.fr/{frey/publications/RR-5052.pdf, Retrieved Jul. 10, 2006).

Axel, Leon, "Biomechanical Dynamics of the Heart with MRI", *Annu. Rev. Biomed. Eng.*, vol. 4, Annual Reviews, pp. 321-347, 2002.

Bathe, Klaus-Jürgen, "Finite element developments for general fluid flows with structural interactions", *Internal Journal for Numerical Methods in Engineering*, vol. 60, John Wiley & Sons, Ltd., pp. 213-232, 2004.

Bloomgarden, Daniel C., "Global Cardiac Function using Fast Breath-hold MRI: Validation of New Acquisition and Analysis Techniques", Williams & Wilkins, pp. 683-692, 1997.

Costa, Kevin D., et al., "Laminar fiber architecture and three-dimensional systolic mechanics in canine ventricular myocardium", American Physiological Society, pp. H595-H607, 1999.

Dang, Alan B.C., et al., "Effect of Ventricular Size and Patch Stiffness in Surgical Anterior Ventricular Restoration: A Finite Element Model Study", *The Society of Thoracic Surgeons*, vol. 79, Elsevier Inc., pp. 185-193, 2005.

Nido, Pedro J. del, "Surgical Management of Right Ventricular Dysfunction Late After Repair of Tetralogy of Fallot: Right Ventricular Remodeling Surgery", *Pediatric Cardiac Surgery Annual*, Elsevier Inc., pp. 1-6, 2006.

Guccione, Julius M., et al., "Finite Element Stress Analysis of Left Ventricular Mechanics in the Beating Dog Heart", *J. Biomechanics*, vol. 28, No. 10, Elsevier Science Ltd., pp. 1167-1177, 1995.

Guccione, J.M., et al., "Passive Material Properties of Intact Ventricular Myocardium Determined From a Cylindrical Model", *Journal of Biomechanical Engineering*, vol. 113, pp. 42-55, 1991.

Guccione, J.M., et al., "Mechanics of Active Contraction in Cardiac Muscle: Part II—Cylindrical Models of the Systolic Left Ventricle", *Journal of Biomechanical Engineering*, vol. 115, pp. 82-90, 1993.

Holzapfel, Gerhard A., et al., "A Layer-Specific Three-Dimensional Model for the Simulation of Balloon Angioplasty using Magnetic Resonance Imaging and Mechanical Testing", *Annals of Biomedical Engineering*, vol. 30, Biomedical Engineering Society, pp. 753-767, 2002.

Holzapfel, Gerhard A., et al., "A New Constitutive Framework for Arterial Wall Mechanics and a Comparative Study of Material Models", *Journal of Elasticity*, vol. 61, pp. 1-48, 2000.

Hunter, Peter, J., "Modeling Total Heart Function", *Annu. Rev. BiomedEng.*, vol. 5, pp. 147-77, 2003.

May-Newman, Karen, et al., "Homogenization Modeling for the Mechanics of Perfused Myocardium", *Progress in Biophysics & Molecular Biology*, vol. 69, pp. 463-481, 1998.

McCulloch, Andrew, et al., "Large-Scale Finite Element Analysis of the Beating Hart", *Critical Reviews in Biomedical Engineering*, vol. 20, No. 5, 6, pp. 427-449, 1992.

Metaxas, Dimitris, N., et al., "Three-Dimiensional Motion Reconstruction and Analysis of the right Ventricle from Planar Tagged MRI", *UMI Microform 9965488*, pp. i-xvii and 1-114, 2000.

Nash, M. P., et al., "Computational Mechanics of the Heart", *Journal of Elasticity*, vol. 61, pp. 113-141, 2000.

Peskin, Charles S., et al., "Cardiac Fluid Dynamics", *Critical Reviews in Biomedical Engineering*, vol. 20, No. 5,6, pp. 451-459, 1992.

Rogers, Jack M., et al., "Nonuniform Muscle Fiber Orientation Causes Spiral Wave Drift in a Finite Element Model of Cardiac Action Potential Propagation", *J Cardiovasc Electrophysiol*, vol. 5, pp. 496-509, 1994.

Sanchez-Quintana, D., et al., "Ventricular Myoarchitecture in Tetralogy of Fallot", *Heart*, vol. 76, pp. 280-286, 1996.

Stevens, Carey, et al., "Sarcomere Length Changes in a 3D Mathematical Model of the Pig Ventricles", *Progress in Biophysics & Molecular Biology*, vol. 82, pp. 229-241, 2003.

Usyk, Taras, et al., "Three Dimensional Electromechanical Model of Porcine Heart with Penetrating Wound Injury", *Medicine Meets Virtual Reality*, vol. 13, pp. 568-573, 2005.

Vetter, Frederick J., et al., "Three-Dimensional Analysis of Regional Cardiac Function: a Model of Rabbit Ventricular Anatomy", *Progress in Biophysics & Molecular Biology*, No. 69, pp. 157-183 (1998).

Vetter, Frederick J., et al., "Three-Dimensional Stress and Strain in Passive Rabbit Left Ventricle: A Model Study", *Annals of Biomedical Engineering*, vol. 28, pp. 781-792, 2000.

Yang, Chun, et al., "In Vivo MRI-Based 3D FSI RV/LV Models for Human Right Ventricle and Patch Design for Potential Computer-Aided Surgery Optimization", *Computers and Structures*, vol. 85, pp. 988-997, 2007.

Rekhter, M.D., et al., "Hypercholesterolemia Causes Mechanical Weakening of Rabbit Atheroma: Local Collagen Loss as a Prerequisite of Plaque Rupture," *Circ. Res.* [online] 2000;86;101-108. [retrieved on Mar. 3, 2010]. Retrieved from the Internet URL: http://circres.ahajournals.org/cgi/contnet/full/86/1/101.

\* cited by examiner

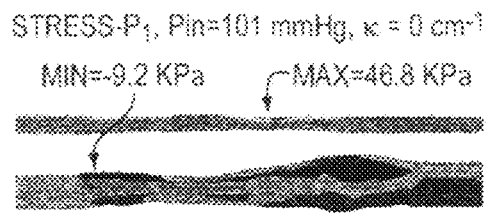
FIG. 13A
FIG. 13B
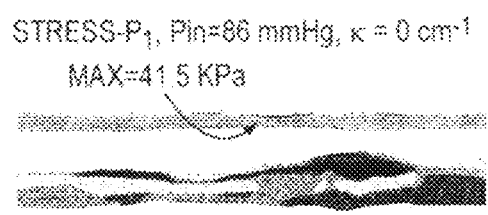
FIG. 13C
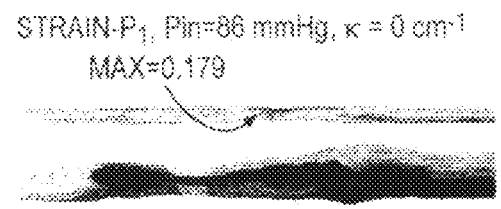
FIG. 13D

FMSS, MODEL 1, Pin=86 mmHg, κ = 0.97 cm⁻¹

MAX FMSS=127.5 dyn/cm²

VELOCITY PLOT, MODEL 1, Pin=86 mmHg, κ = 0.97 cm⁻¹
FLOW                    MAX VELOCITY=69.5 cm/s

FMSS, MODEL 2, Pin=86 mmHg, NO BENDING

MAX FMSS=108.4 dyn/cm²

VELOCITY PLOT, MODEL 2, Pin=86 mmHg, NO BENDING
FLOW      MAX VELOCITY=76.3 cm/s

MIN      UNIVERSAL SCALE      MAX

AUTOMATIC VASCULAR MODEL GENERATION BASED ON FLUID-STRUCTURE INTERACTIONS (FSI)

RELATED APPLICATION(S)

This application is the U.S. National Stage of International Application No. PCT/US2010/024527, filed Feb. 18, 2010, which designates the U.S., published in English, and claims the benefit of U.S. Provisional Application No. 61/208,501, filed Feb. 25, 2009. The entire teachings of the above applications are incorporated herein by reference.

GOVERNMENT SUPPORT

The invention was supported, in whole or in part, by a grant DMS-0540684 from the National Science Foundation and a grant NIH/NIBIB, 1 ROI EB004759 from the National Institutes of Health. The Government has certain rights in the invention.

BACKGROUND OF THE INVENTION

Cardiovascular disease (CVD) is the No. 1 killer in the United States. More than 60% of all myocardial infarctions are caused by rupture of a vulnerable plaque. A large number of victims of the disease, who are apparently healthy, die suddenly without prior symptoms. About 95 percent of sudden cardiac arrest victims die before reaching a hospital. About 250,000 people a year die of coronary artery disease (CAD) without being hospitalized.

However, the mechanisms causing plaque rupture responsible for a stroke or cardiac arrest are poorly understood, and available screening and diagnostic methods are insufficient to identify the victims before the event occurs. For example, current technology for diagnosis of applicable cardiovascular diseases (e.g., carotid plaque rupture, coronary plaque rupture and aneurysm rupture) generally lacks accurate and reliable computational mechanical analysis. Clinically available magnetic resonance imaging (MRI), computed tomography (CT), and ultrasound medical image equipment do not have computational mechanical analysis and related predictive computational indices for physicians to use in their decision making process. Even if some of the equipment may have some measurement data derived from some computational models, those models are overly simplified. The state of the art clinical decision making process is still based on morphologies derived from medical images with experiences from medical practice. Some two-dimensional (2D) MRI-based models and three-dimensional (3D) structure-only or fluid-only models have been known in the art. However, they are not generally adequate for decision-making purposes. In those models, mechanical analysis is either ignored or performed based on deficient models.

Therefore, a need exists for developing models adequate for decision-making purposes.

SUMMARY OF THE INVENTION

A computer system and method are disclosed for automatically generating a vascular model of a blood vessel to support, for example, identification of mechanical factors (including quantitative indices) corresponding to the blood vessel.

An embodiment of the invention is a computer-implemented method of automatically generating a vascular model of a blood vessel. Data points corresponding to a contour of a blood vessel are interpolated. A 3D structural model, representing 3D structural characteristics of the blood vessel, and a 3D fluid model, representing 3D characteristics of fluid flow within the blood vessel, are generated based on respective interpolated contours. A vascular model is generated based on the structural and fluid models.

The method may be performed in order to identify mechanical factors corresponding to the blood vessel. The data points may be collected by an imaging technique, such as magnetic resonance imaging (MRI) or ultrasound (e.g., intravascular ultrasound), in embodiments of the invention.

The method may also include performing a mechanical analysis of the vascular model to identify a factor associated with the vessel, such as a factor relating to a plaque in the vessel or a potential plaque rupture condition.

In an embodiment, the vascular model represents 3D fluid-structure interactions (FSI) in the blood vessel. In some embodiments, the blood vessel may be an artery, such as a coronary artery or a carotid artery.

The vascular model may include plaque components. The method may include calculating structure stress and/or strain (hereinafter referred to as "stress/strain") and flow shear stress. The method may be performed by an operator using a digital computer and may include generating 2D and 3D mechanical stress/strain distributions. The method may also include generating 2D and 3D flow shear stress distributions. The data points may be geometric data. The method transforms input data, such as the data points, and produces output data, such as the calculated 2D and 3D mechanical stress/strain and flow shear stress distributions. In some embodiments, identifying mechanical factors includes identifying quantitative indices, such as maximum stress/strain and maximum flow shear stress, corresponding to disease state of the blood vessel.

In another embodiment, the invention provides a computer system comprising a data source containing a plurality of data points corresponding to a contour of a blood vessel and a modeler coupled to receive data from the data source, the modeler interpolating the plurality of data points to yield an interpolated contour. The modeler further generates a structural model, a fluid model, and a vascular model based on the structural model and the fluid model. The structural model represents three-dimensional structural characteristics of the blood vessel, based on respective interpolated contours. The fluid model represents three-dimensional characteristics of fluid flow within the vessel, based on respective interpolated contours.

Advantageously, Applicant's invention employs a 3D model of a blood vessel that includes fluid-structure interactions (e.g., blood-vessel interactions) and the structure of the vessel. The 3D models of the invention further include various components of the vessel, e.g., various plaque components for atherosclerotic plaques. Therefore, the invention can automatically and accurately model mechanical distribution(s), such as stress/strain distribution(s), in the vessel under investigation. Also, Applicant's invention can identify a factor, such as a mechanical biological index, to quantify the degree of the disease status, which can help physicians in decision-making processes.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 8a is a perspective view of a 3D structural mesh of a vessel bifurcation. FIG. 8b is a perspective view of the 3D fluid mesh corresponding to the structural mesh of FIG. 8a. FIG. 8c is a perspective view of a cut surface of a 3D structural mesh for an artery showing plaque components. FIG. 8d is a perspective view of the 3D fluid mesh corresponding to the structural mesh of FIG. 8c.

FIGS. 13a-13d show Stress-$P_1$ and Strain-$P_1$ distributions from a model (Model 2 with no cyclic bending) that show only modest variations caused by imposed pulsating pressure conditions.

DETAILED DESCRIPTION OF THE INVENTION

A description of example embodiments of the invention follows.

Embodiments of the invention are referred to as MRI-based Mechanical Vulnerable Plaque Analysis ($M^2$VPA), although the techniques described herein are applicable to other forms of data than MRI (e.g., computed tomography, ultrasound, and optical imaging) and may be used for additional purposes than plaque analysis (e.g., modeling of ventricles, aneurisms, and other blood vessels). An embodiment of the invention generates a three-dimensional (3D) model of a blood vessel (i.e., a vascular model) via a 3D geometry reconstruction technique that processes multiple two-dimensional (2D) data "slices." The model construction (generation) process is automated in an embodiment of the invention. The blood vessel may be an artery, such as a coronary artery, carotid artery, or aorta. The artery may contain a plaque that is characteristic of atherosclerosis.

The term "model" as used herein includes the geometry of the vessel, including its components, such as a plaque; a procedure to adjust the geometry; mesh; material; mathematical equations; and a procedure to perform the solution procedure.

Because plaques have complex irregular geometries with component inclusions, which are challenging for generation of a 3D vascular model (mesh), a component-fitting mesh generation technique is used to generate a mesh for the models. The reconstruction technique is capable of dealing with multi-component structures and complex geometries, such as vascular bifurcation (forking of vessels). Using this technique, the 3D plaque domain is divided into hundreds of small "volumes" to curve-fit irregular plaque geometry and plaque component inclusions. Mesh analysis is performed by iteratively decreasing mesh density by 10% in each dimension until solution differences are less than 2%. The resulting mesh is then used for computational simulations.

The generated model enables further mechanical analysis to identify critical mechanical stress/strain conditions which might be related to plaque rupture in the vessel. Previously, methods or apparatuses for automatically constructing a 3D vascular model for further mechanical analysis as in the present invention have not been available.

Embodiments of the invention provide a platform for fast reconstruction of complex structures, either in component or shape, whose contours are obtained from medical images. Efficiency of embodiments of the invention has been tested by real-life simulations with data from in vivo/ex vivo magnetic resonance (MR) images of a human atherosclerotic carotid artery and a coronary artery.

Figure 1:
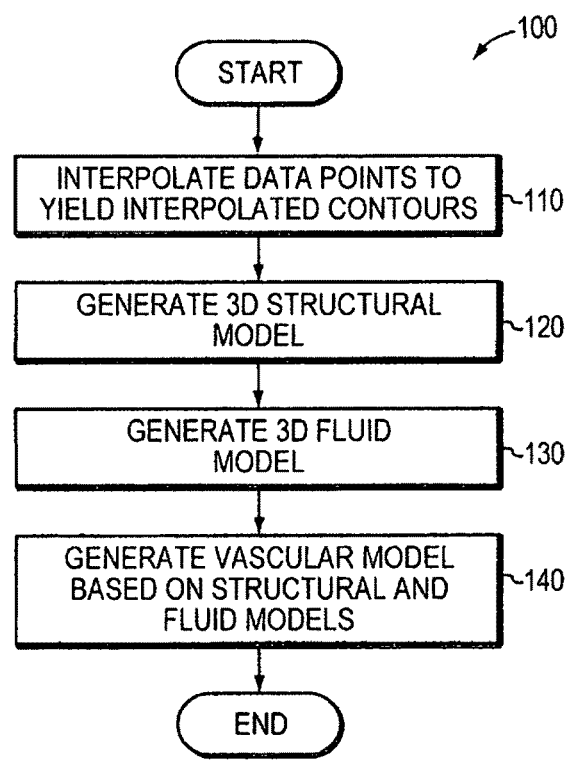
FIG. 1 is a flow diagram of an embodiment of the invention.

FIG. 1 is a flow diagram of an embodiment 100 of the invention, which is a process that transforms raw data into a 3D vascular model, i.e., a model representing 3D characteristics of a blood vessel including fluid-structure interactions (FSIs). The raw data may include contour data describing the geometric configuration of plaques within the blood vessel, as well as material properties and other indicators such as blood pressure. Data points corresponding to a contour of a blood vessel are interpolated (110) to yield an interpolated contour. Such interpolation occurs for various contours in a 2D slice of data, which may be obtained via an earlier data collection step. A structural model, representing three-dimensional structural characteristics of the blood vessel, is generated (120) based on multiple interpolated contours corresponding to different 2D slices. A fluid model that represents 3D characteristics of fluid flow within the vessel is also generated (130). Finally, a vascular model is generated (140) based on the structural model and the fluid model. In some embodiments, the vascular model represents 3D fluid-structure interactions (FSIs) and enables further mechanical analysis of the vessel and of one or more plaques within the vessel.

The mechanical analysis may be used to produce an assessment of the vulnerability of a plaque rupture in order to diagnose, assess, or treat a medical condition, such as cardiovascular disease (CVD). Generally, plaque rupture involves many controlling factors. For example, mechanical forces, structural features, and material properties can affect mechanical forces in plaques, which determine the vulnerability of the plaques to rupture. Examples of such mechanical forces include blood pressure, shear stress, stretch, residual stress, tethering, and motion. Examples of structural features include plaque morphology, vessel geometry, vessel thickness, lumen, plaque components, lipid shape and size, cap thickness, calcification, hemorrhage, and surface weakening. Examples of material properties include material parameters for vessel and plaque components, such as fibrous caps, lipids and calcification, luminal surface weakening or erosion. The computational 3D models of the invention capture the major controlling factors affecting mechanical forces in the plaque(s). Preferably, patient-specific data, for example, blood pressure, vessel geometry, plaque morphology, plaque components and the like, are employed in the invention.

Figure 2:
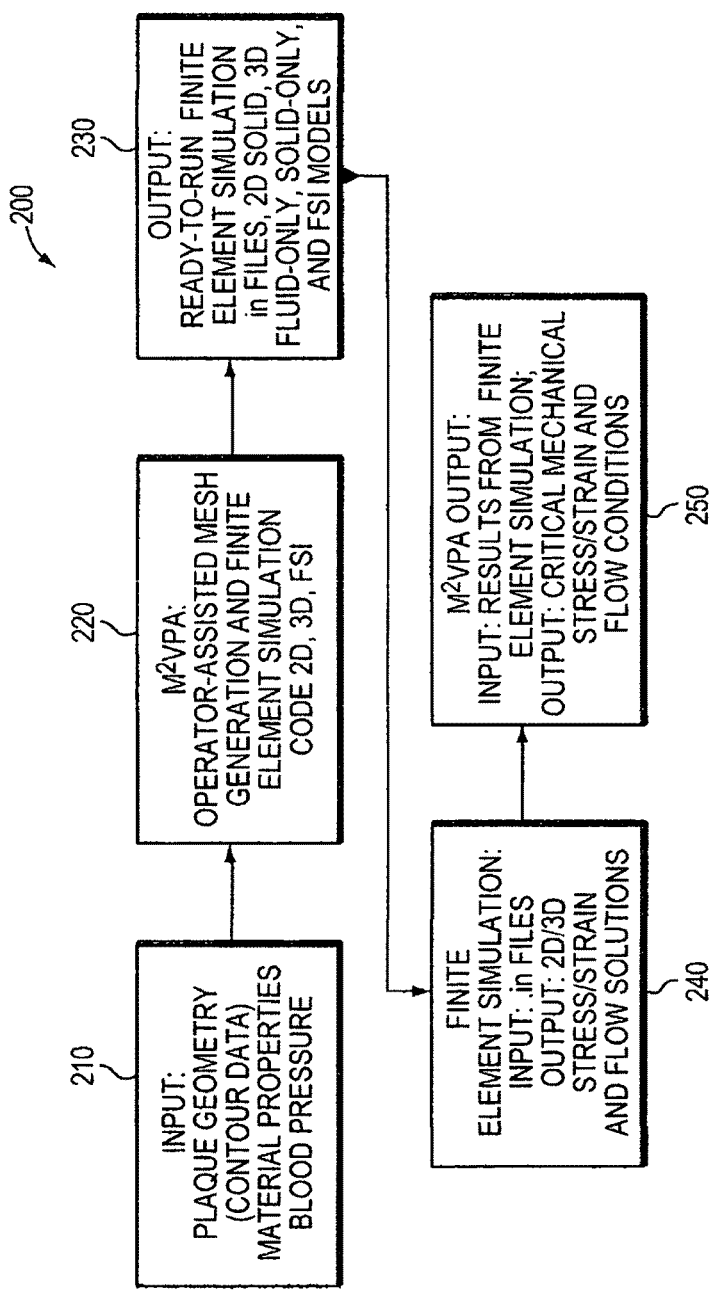
FIG. 2 is a flow diagram showing an end-to-end analytical framework in accordance with an embodiment of the invention.

FIG. 2 is a flow diagram showing an end-to-end analytical framework in accordance with an embodiment 200 of the invention. In this framework, M²VPA is one component of the framework, along with input data and a finite element simulation software, such as the commercial finite-element package ADINA® (Adina R&D, Inc., Watertown, Mass., USA). Data corresponding to plaque geometries, i.e., contour data, as well as material properties and blood pressure, are input for processing (210). Known user interface techniques for prompting user entry of these data are utilized. M²VPA performs operator-assisted automatic mesh generation (220) using a technical computing environment, such as MATLAB® (The Mathworks, Inc. Natick, Mass., USA) and exports ready-to-run simulation data, such as ADINA®-readable data, for 2D solid, 3D solid-only, 3D fluid-only, and vascular (FSI) models (230). The finite element simulation software performs computational simulations, e.g., to compute 2D/3D stress and strain and flow solutions (240), and M²VPA performs critical mechanical analysis (250), e.g., to identify critical stress and strain and flow conditions related to potential plaque ruptures. In one embodiment, the computational simulations employ model equations of Tang, D., et al. *Mechanical Image Analysis Using Finite Element Method*, Carotid Disease: The Role of Imaging in Diagnosis and Management, C. Cambridge University Press: pp. 323-339 (2006); Tang D., et al. *Quantifying Effects of Plaque Structure and Material Properties on Stress Behaviors in Human Atherosclerotic Plaques Using* 3D PSI Models, J. Biomech. Eng., 127(7):1185-1194 (2005); Tang, D., et al. *Local Maximal Stress Hypothesis and Computational Plaque Vulnerability Index for Atherosclerotic Plaque Assessment*, Ann. Biomed. Eng., 33(12):1789-1801 (2005); Tang, D., et al. *3D MRI-Based Multi-Component FSI Models for Atherosclerotic Plaques a* 3-*D FSI model, Ann. Biomed. Eng.*, 32(7), pp. 947-960 (2004); Tang, D., et al. *In Vivo/Ex Vivo MRI-Based 3D Models with Fluid-Structure Interactions for Human Atherosclerotic Plaques Compared with Fluid/Wall-Only Models*, CMES: Comput. Model. Eng. Sci. 19(3):233-245 (2007); Tang, D., *Flow in Healthy and Stenosed Arteries,*" Wiley Encyclopedia of Biomedical Engineering, Article 1525: pp. 1-16, New Jersey, John Wiley & Sons, Inc. (2006); Tang, D., et al. *A Viscoelastic Model and Meshless GFD Method for Blood Flow in Collapsible Stenotic Arteries*, Advances in Computational Engineering & Sciences, Chap. 11, International Conference on Computational Engineering and Sciences, Norcross, Ga., Tech Science Press (2002); Tang, D., et al. *Effects of Stenosis Asymmetry on Blood Flow and Artery Compression: a 3-D FSI Model*, Ann. Biomed. Eng., 31:1182-1193 (2003); Tang, D., et al., *Effect of a Lipid Pool on Stress and strain Distributions in Stenotic Arteries: 3D FSI Models,*" J. Biomech. Eng., 126: 363-370 (2004); and Tang, D., et al., *Patient-Specific Artery Shrinkage and 3D Zero-Stress State in Multi-Component* 3*D FSI Models for Carotid Atherosclerotic Plaques Based on In Vivo MRI Data*, Journal of Molecular & Cellular Biomechanics, Special Volume dedicated to Y. C. Fung's 90th birthday, 337-350 (2008), the entire teachings of which are incorporated herein by reference. Further details of model construction and data analysis are found in International Patent Application No. PCT/US2005/044085, filed Dec. 8, 2005, the entire teachings of which are hereby incorporated by reference.

Figure 3:
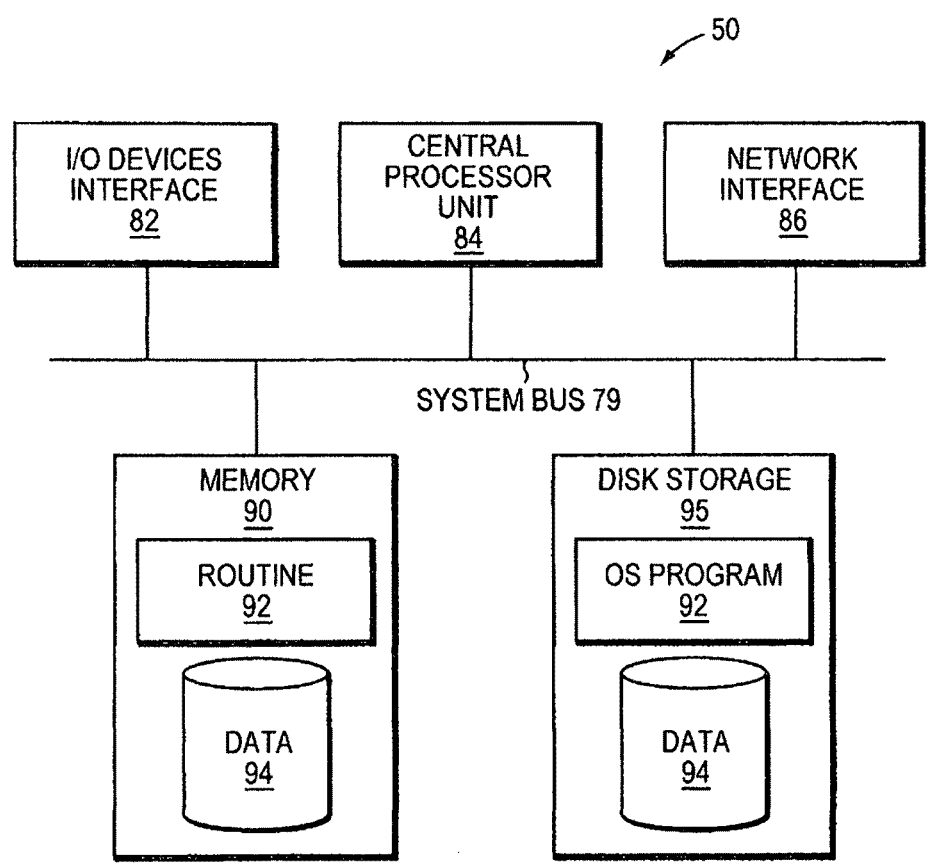
FIG. 3 is a block diagram of a computer system in which embodiments of the present invention are deployed.

FIG. 3 is a block diagram of a computer system in which embodiments of the present invention are deployed. A computer 50 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50. Network interface 86 allows the computer to connect to various other devices attached to a network (e.g., a wide area network, a local area network or global computer network). Memory 90 provides volatile storage for computer software instructions 92 and data 94 used to implement an embodiment of the present invention (e.g., elements of embodiments 100, 200 detailed above and in FIGS. 1 and 2 and modules 410, 420, 430, 440 of FIG. 4). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

Figure 4:
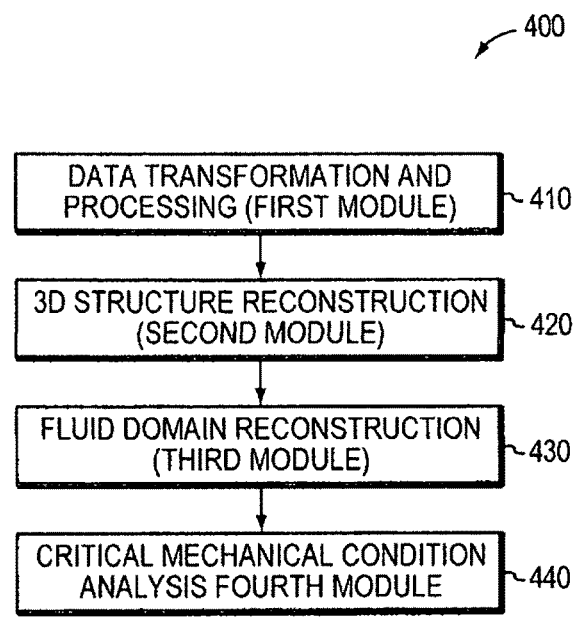
FIG. 4 is a block diagram of the main modules of an embodiment of the invention that is a computer-based system.

FIG. 4 is a block diagram of the main modules of an embodiment 400 of the invention. The four main modules are: (1) a first module 410 for data transformation and processing; (2) a second module 420 for 3D structure reconstruction; (3) a third module 430 for fluid domain reconstruction; and (4) a fourth module 440 for critical mechanical condition analysis.

The first module 410 performs data input and pre-processing, including interpolation of data points along contours. The second module 420 creates component-fitting lines and surfaces for each 2D slice, connects slices, makes surfaces linking slices, and forms component-fitting volumes; generates a mesh for every volume created; and assigns material properties to each volume. The third module 430 is similar to the second module 420, but applies to the fluid domain. The second module 420 and the third module 430 generate data used to solve a 3D fluid-structure interaction (FSI) model. Typically, modules 420 and 430 generate a 3D mesh for the 3D FSI model. The mesh is typically used as an input to a finite element simulation package, which then solves the 3D FSI model. In an embodiment, the finite element package is the commercial finite-element package ADINA® (ADINA R&D, Inc., Watertown, Mass., USA). Modules 420 and 430 can generate ADINA®-ready input files. The fourth module 440 performs further mechanical analysis to identify critical mechanical and morphological conditions which may be relevant to plaque rupture. Processing in the four modules 410, 420, 430, and 440 is automated in one embodiment. In one embodiment, an operator provides inputs to control the processing.

Figure 5A:
FIGS. 5a-5e show a human coronary atherosclerotic plaque sample that may be used in accordance with an embodiment of the invention: (a) magnetic resonance (MR) image with T1 weighting; (b) MR image with middle-T2 weighting; (c) MR image with T2 weighting; (d) Contour plot of a segmented image using a multi-contrast algorithm; (e) Histological data.
Figure 5B:
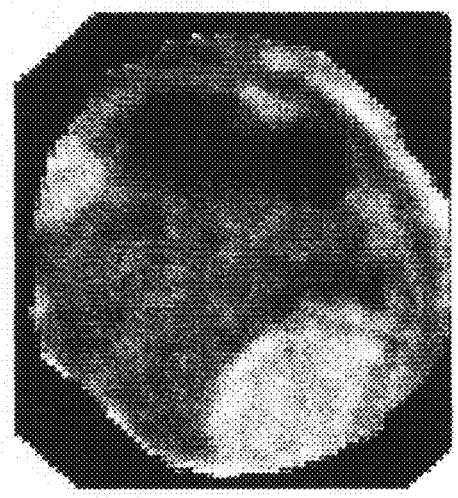
Figure 5C:
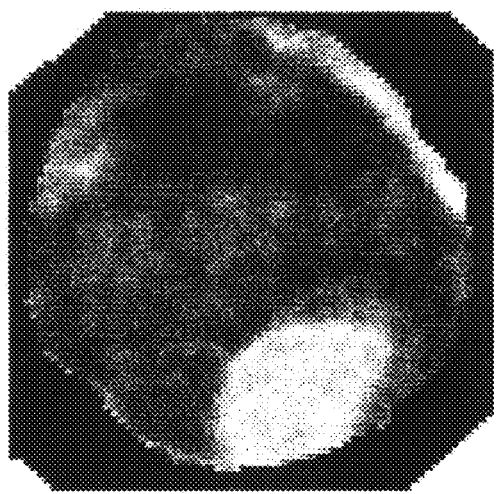
Figure 5D:
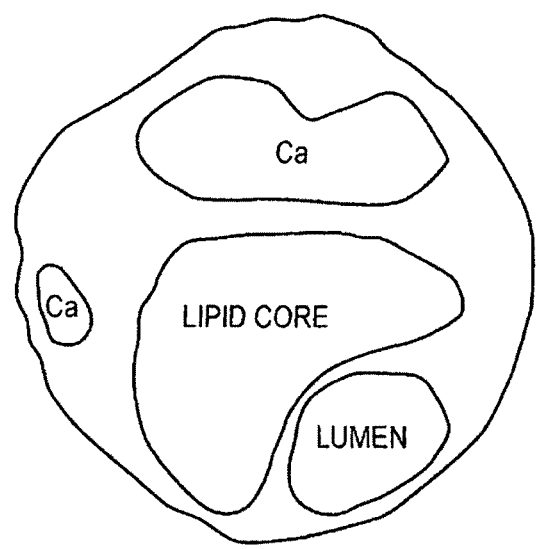
Figure 5E:
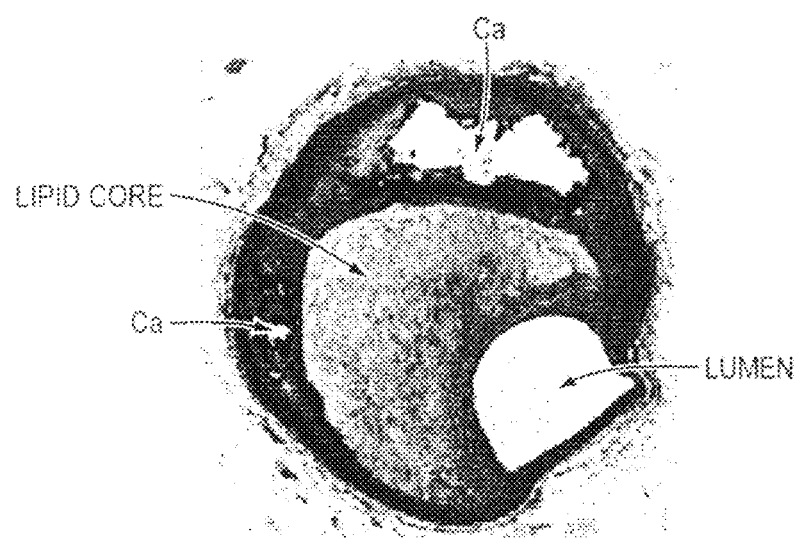

FIGS. 5a-5e show a human coronary atherosclerotic plaque sample that may be used in accordance with an embodiment of the invention. FIGS. 5a-5c show MR images with T1, middle-T2, and T2-weightings, respectively. The 2D slice shown was selected from a 36-slice data set of a human coronary plaque sample. FIG. 5d shows plaque component contour plots based on histological segmentation data, and FIG. 5e shows corresponding histological data.

Figure 6A:
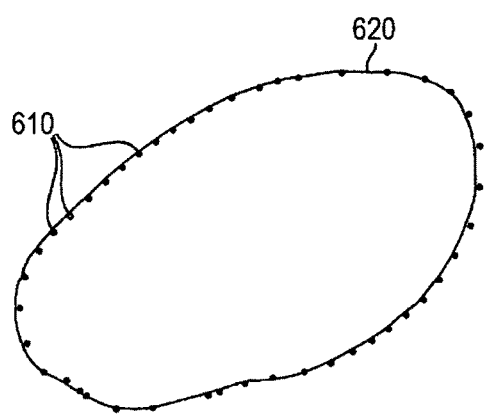
FIGS. 6a-b show interpolated contours and boundary lines in accordance with an embodiment of the invention.
Figure 6B:
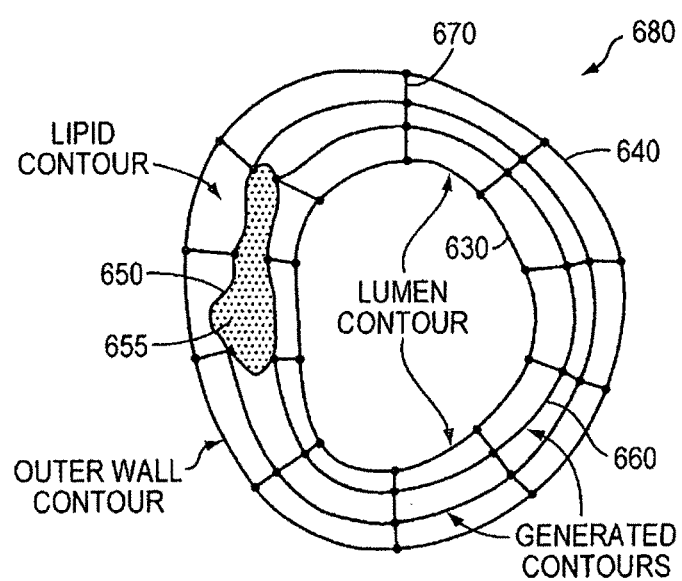

FIGS. 6a-b show interpolated contours and boundary lines in a 2D slice 680 in accordance with an embodiment of the invention. FIG. 6a shows data points 610 in a contour and an interpolated contour 620, obtained using cubic spline interpolation in an embodiment. For an atherosclerotic artery, the raw data points (prior to interpolation) may correspond to a lumen contour 630, an outer arterial wall contour 640, a lipid contour 650, or the contour of a calcified structure (not shown) of FIG. 6b. Interpolation is performed to bridge gaps and to correct for irregular shapes caused by image and segmentation distortion. The data points 610 may be collected and segmented from a medical image, such as a magnetic resonance (MR), computed tomography (CT), or an ultrasound (e.g., intravascular ultrasound, "IVUS") image, prior to interpolation. Data are imported, segmented, and interpolated in the first module 410.

If in vivo medical images are used for the 3D reconstruction, since the artery is pressurized and axially stretched, the contours 630, 640 of lumens and outer walls need to be shrunk or expanded at a certain rate. An embodiment of the invention determines the shrink rate in two directions (axial and circumferential) so that when the structure is pressurized with the mean pressure value, the deformed lumen contours 630 and outer wall contours 640 have the best match with original contours while keeping the volume before and after shrinking unchanged. The shrunken geometry is used as the starting shape for numerical simulation.

To support the generation of a solid (structural) model of the blood vessel, the cross section of each 2D slice is divided into several parts circumferentially by annular lines, shown as generated contours 660 in FIG. 6b. Part of the generated contour 660 is used to fit the contour of a component such as a lipid (e.g., lipid contour 650 for lipid 655) or calcification, if present. In an embodiment, an axial interpolation along the blood vessel is performed, e.g., using a cubic spline interpolation, to generate extra slices to avoid sudden geometric changes due to angiography gaps.

A 3D solid (polyhedron) is enclosed by facets (also referred to as surfaces or faces), and a facet is composed of edges. The second module 420 creates radial lines 670 as the edge of a surface for a volume. Due to the complexity of the geometry, the slice 680 is divided into several areas, and a different mesh density is assigned for each area. In an embodiment, many lines (generally poly lines which are series of connected line segments, i.e., not necessarily straight lines) are created for each slice. In an embodiment of the invention, lines can be copied between different slices as long as the target slice has the same topological structure as the source slice. Generated contours 660 are used to correlate topological structures of slices below and above a bifurcation (forking of a vessel). In one embodiment, lines in respective slices above and below a bifurcation are drawn manually by an operator, and lines in other slices are cloned from the slices above and below the bifurcation.

Figure 7A:
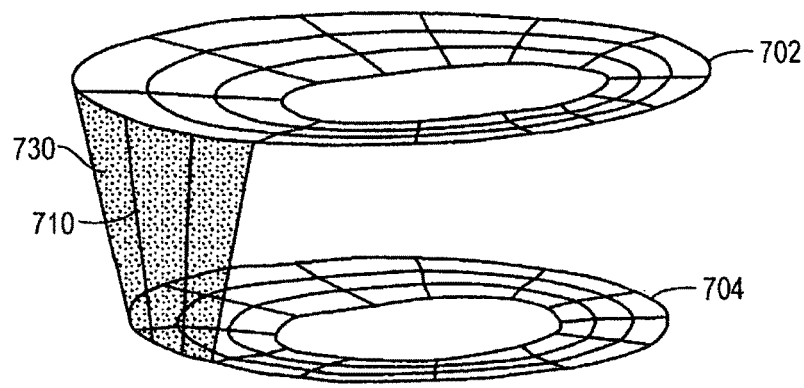
FIGS. 7a-b illustrate an association between neighboring 2D slices used to generate a 3D model.
Figure 7B:
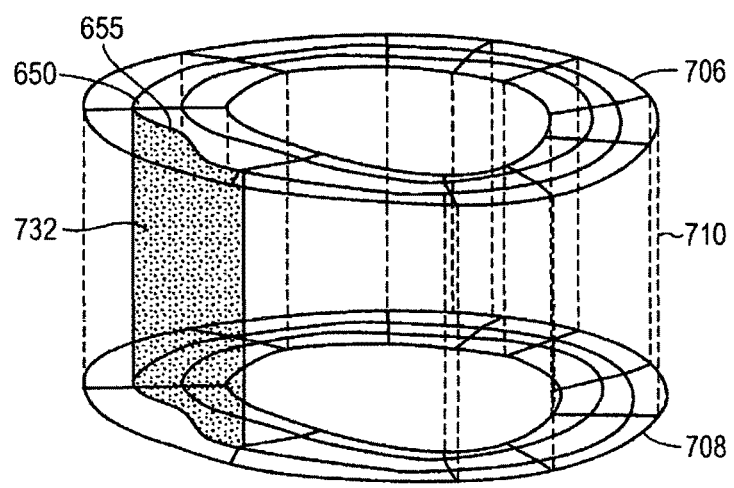

FIGS. 7a and 7b illustrate an association between respective neighboring 2D slices 702, 704 and 706, 708, respectively, used to generate a 3D model. Inter-slice lines 710 are generated automatically. Intra-slice lines (e.g., lines corresponding to generated contours 660 and radial lines 670) and inter-slice lines 710 are used to assemble surfaces such as surface 730. As shown in FIG. 7b, 2D slices 706 and 708 may include generated contours 660 that are component contours, such as lipid contour 650 for lipid 655. Advantageously, the radial curvature of component contours, such as contour 650, is automatically captured in a smooth line to curve-fit the irregular component geometry. Generated contours 660, including component contours 650 and radial lines 670, and inter-slice lines 710 are used to assemble surfaces such as surface 732. In an embodiment, surfaces such as surfaces 730 and 732 are generated automatically. Volumes may also be generated automatically. In an embodiment, the 3D plaque domain is automatically divided into a number of small volumes to capture the irregular plaque geometry, including plaque component inclusions, such as lipid 655.

In an embodiment, six neighboring surfaces are used to assemble a volume, i.e., forming a hexahedron. Each volume is assigned a material model corresponding to the tissue type the volume represents. All structural information, including data points, lines, surfaces, and volumes, is exported to serve as an input to a finite element simulation package. In an embodiment, the finite element package is the commercial finite-element package ADINA® (ADINA R&D, Inc., Watertown, Mass., USA). Thus, the second module 420 generates a 3D structural model of the vessel.

In the third module 430, the lumen contours of the structural model are extracted to be the boundary of the fluid domain. Similar steps as in the second module 420 are followed in the third module 430 to create lines, assemble surfaces, and generate volumes for the fluid domain. In one embodiment, extra points (assistant points) are created for the fluid model. The third module 430 also creates geometric parts related to fluid modeling, such as leader-follower and slipping lines, which are also used for modeling fluid-structure interactions (FSIs). Fluid domain information is exported to serve as an input file to a finite element simulation package, such as ADINA®. Thus, the third module 430 generates a 3D fluid flow model for the vessel.

Figure 8A:
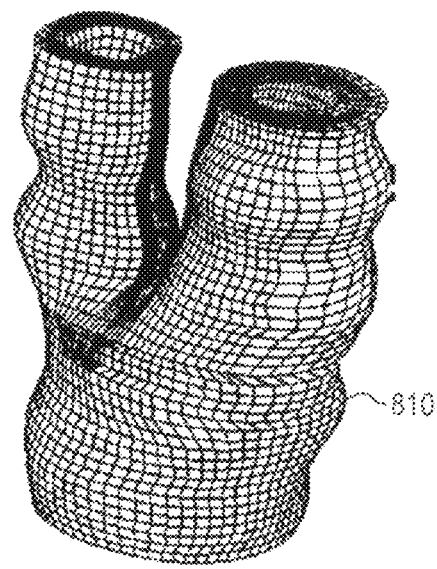
FIGS. 8a-8d illustrate generated meshes for 3D models: (a), (c) 3D structural meshes; (b), (d) 3D fluid meshes.
Figure 8B:
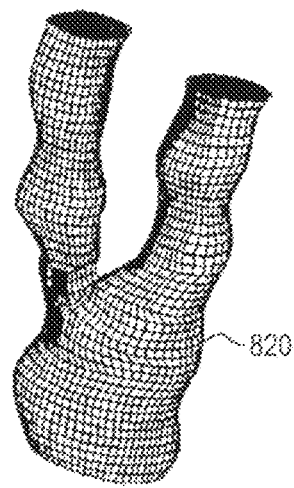
Figure 8C:
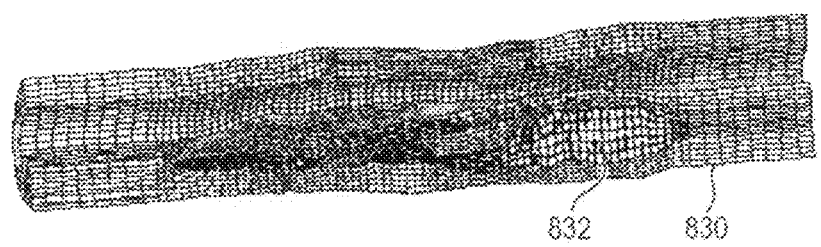
Figure 8D:
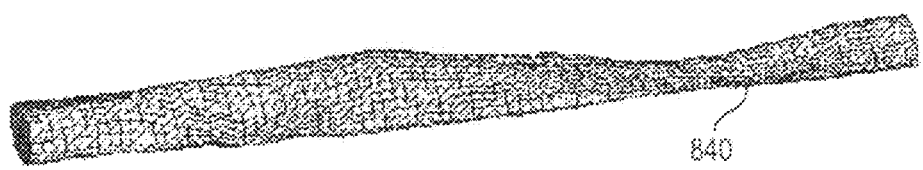

FIGS. 8a-8d illustrate 3D meshes of 3D models generated by above mentioned modules 420 and 430. FIG. 8a is a perspective view of 3D structural mesh 810 of a vessel bifurcation and FIG. 8b is a perspective view of corresponding 3D fluid mesh 820. FIG. 8c is a perspective view of a cut surface of 3D structural mesh 830 for an artery showing plaque component mesh 832. FIG. 8d is a perspective view of 3D fluid mesh 840 corresponding to structural mesh 830. The 3D FSI models are solved by a finite element simulation software package, such as ADINA®, in response to input files formed by modules 420 and 430. ADINA® uses unstructured finite element methods for both the structural (solid) model, including, e.g., mesh 810 in FIG. 8a, and the fluid model, including, e.g., mesh 820 in FIG. 8b. Numerous small volumes as described above fit the entire solid geometry, as shown in FIG. 8a.

After both the structural model, including, e.g., meshes 810 and 830, and the fluid model, including, e.g., meshes 820 and 840, have been constructed, boundary conditions (e.g., fixed points), loading, and other simulation controls (e.g., time functions and time steps) are added to the model in an embodiment to yield a vascular model. Finally, fluid-structure interactions (FSIs) are simulated in an embodiment. Nonlinear, incremental, iterative procedures can be used to handle FSIs. The governing finite element equations for both the solid and fluid models can be solved by, for example, the Newton-Raphson iteration method. A proper computer mesh is chosen to fit the shape of components, vessels, and the fluid domain that are included in the 3D model of the vessel.

In case of a problem with mesh generation, contour shapes and lines, such as contour 650, FIG. 7b, may be geometrically adjusted to provide a better mesh. For example, for a 3D model of plaques, a finer mesh can be used for thin plaque caps and components with sharp angles to get better resolution and to handle high stress concentration behaviors. FIG. 8c illustrates different mesh densities in solid mesh 830 for a 3D model of an artery that includes component mesh 832. Component mesh 832 may be for a plaque component, such as a calcification or a lipid core of a coronary plaque, as shown in FIG. 5e. Several tools are provided to eliminate or mitigate sharp angles by adjusting inter-slice and intra-slice lines and the shapes of generated contours 660, FIG. 6b, including component contours 650, FIGS. 6b and 7b. An optimization tool is also provided to determine the coordinates of extra assistant points for the fluid domain.

The 3D solid and fluid models, including, e.g., meshes 830 and 840, of a vessel, such as an artery, can be stretched axially and pressurized gradually to specified conditions. Unsteady simulation, for example, under pulsating pressure conditions, can then be followed. Typically, mesh analysis is performed until differences between solutions from two consecutive meshes are negligible (e.g., less than about 1% using a proper vector norm).

In an embodiment, the computational results, such as maximal principal stress and strain in the structure and shear stress in the fluid domain, are extracted from the finite element simulation results for further mechanical analysis. In an embodiment, the results are extracted from an ADINA® output file for further mechanical analysis. By tracing values at each selected point, the fourth module 440 provides tools to display mechanical parameters at critical sites, such as where a fibrous cap is locally thin, during a cardiac cycle. The values of the simulation results at any point of the 3D structural and fluid model may be tracked. The tracking points may include integration points.

Figure 9:
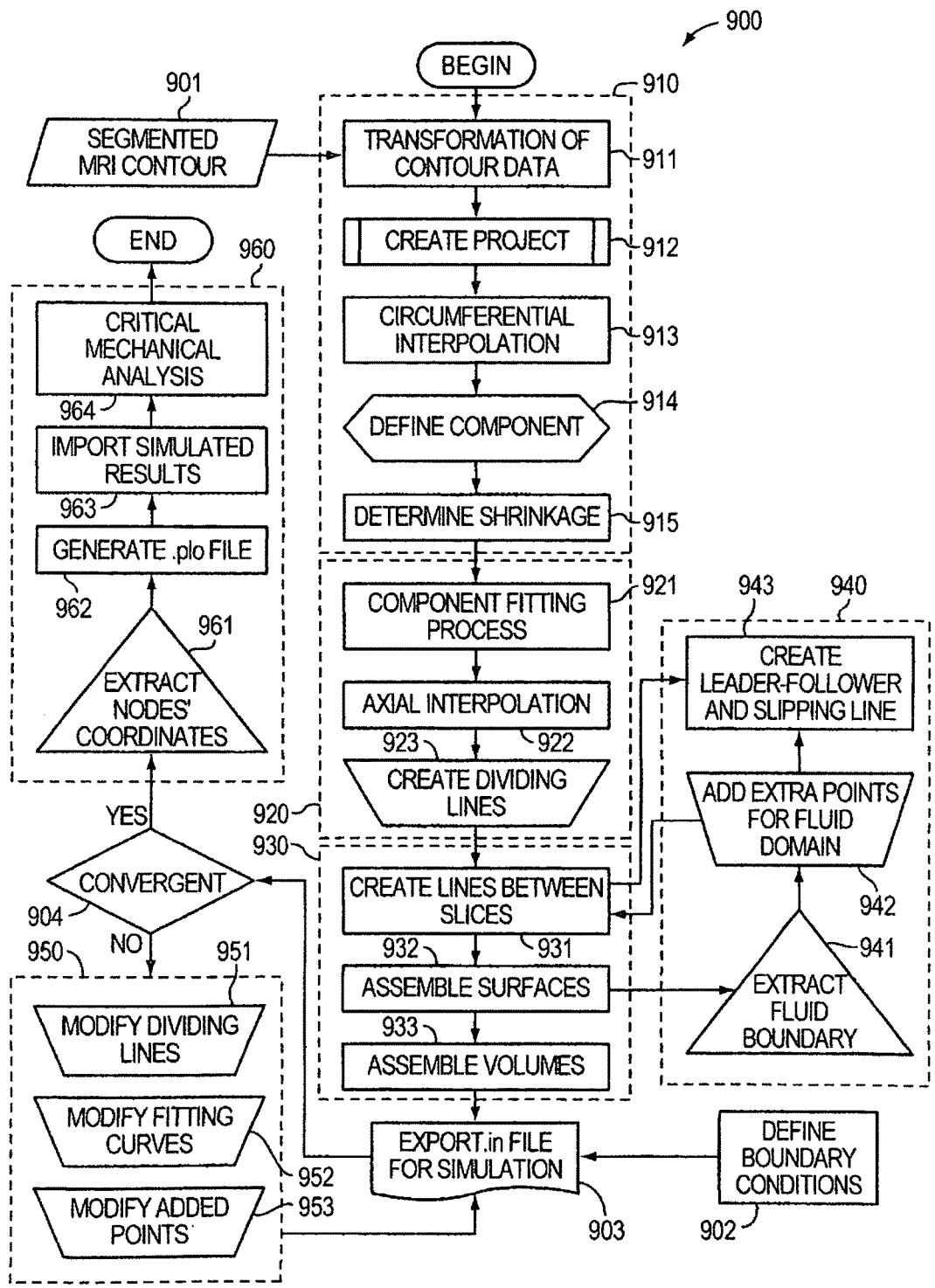
FIG. 9 is a flow diagram showing detailed processing in an end-to-end process according to an embodiment of the invention.

FIG. 9 is a flow diagram showing detailed processing in an end-to-end process 900 according to an embodiment of the invention. Segmented contour data (e.g., MRI data) is provided as input (901).

Subprocess 910 performs data transformation and processing. Segmented contour data is imported and transformed for further processing (911). After a project is created (912), circumferential interpolation is performed (913), as discussed above with reference to FIG. 6a and module 410. Components are defined (914), and shrinkage is determined (915).

Subprocess 920 processes contours and divides areas in 2D slices. Components are fitted (921), axial interpolation is performed (922), and dividing lines are created (923), as discussed above with reference to FIG. 6b and module 420.

Subprocess 930 performs 3D curve-volume fitting. Inter-slice lines are created (931), and surfaces (932) and volumes (933) are assembled, as discussed above with reference to FIGS. 7A-7B and module 420.

Subprocess 940 performs fluid domain reconstruction, as discussed above with reference to module 430. A fluid boundary is extracted from a structural model (941). Extra points are added for the fluid domain (942), and leader-follower and slipping lines are created (943).

Boundary conditions are defined (902), and output from 3D structural and fluid models of subprocesses 920, 930, 940 are exported to the finite element simulation package (903). If mesh generation converges (904), further mechanical analysis may be performed in subprocess 960, as discussed above with respect to module 440. In case of non-convergence, subprocess 950 performs optional geometry adjustment, in which modifications may be made to dividing lines, fitting curves, and added points (951, 952, 953, respectively).

Subprocess 960 performs post-processing for mechanical analysis, as discussed above with reference to module 440. Coordinates from nodes in the 3D vascular model are extracted (961). A command file is generated (962) to extract simulation results of interest from simulation results (963). Further critical mechanical analysis is performed by step 964.

Details of laboratory testing, validation, and models employed in accordance with embodiments of the invention are presented by a case study below.

Mechanical Testing of Vessel Material Properties

A coronary artery was obtained from Washington University Medical School with consent obtained. After the connective tissue was removed, the artery was cut to open. Dumbbell-shaped strips of 2 mm width were cut in the axial and radial directions. The strips were cut from areas without obvious plaque blocks to avoid the disturbance to the experimental data. Pieces of water-proof sand paper were attached on the ends of each strip with cyanoacrylate adhesive. Then two black markers were put in the central area for non-contact deformation measurement. Samples were submerged in a 37° C. thermostatic saline bath and mounted on a custom-designed device to perform uniaxial tests. For each test, after 5 pre-conditioning cycles to a stretch ratio of 1.3, the sample was cycled three times with stretch ratio varying from 1.0 to 1.3 at a rate of 10% per minute. Force was measured using an isometric torque transducer (0.15 N-m, Futek) attached to the sample via a 7.6 cm plexiglass arm extending out of the bath yielding ±4 mN accuracy. Engineering stress was calculated by dividing force by the initial cross-sectional area of the sample measured with a micrometer (±10 μm).

MRI Data Acquisition

A 3D MRI data set obtained from a human coronary plaque ex vivo consisting of 36 slices with a relatively high resolution (0.25 mm×0.23 mm×0.5 mm) was used as the baseline case to develop the computational model. The specimen was fixed in a 10% buffered formalin solution and placed in a polyethylene tube and then stored at 4 degrees C. within 12 hours after removal from the heart. MRI imaging was taken within 2 days at room temperature. As described above with respect to FIGS. 5a-e, multi-contrast (T1, middle-T2, T2, and proton density-weighting) MRI imaging was performed to better differentiate different components in the plaque.

Individual contour plots, such as FIG. 5a, show that T1-weighting is better to assess calcification, T2-weighting is better to assess the lumen and outer boundary, and the middle-T2 weighting is better for lipid core assessment. The MR system was a 3T Siemens Allegra clinical system (Siemens Medical Solutions, Malvern, Pa.). A single-loop volume coil (Nova Medical, Inc, Wilmington, Mass.) with a diameter of 3.5 cm was used as a transmitter and receiver. After completion of the MR study, the transverse sections with a thickness of 10 μm were obtained at 1 mm intervals from each specimen. These paraffin embedded sections were stained with hematoxylin and eosin (H&E), Masson's trichrome, and elastin van Gieson's (EVG) stains to identify major plaque components: calcification (Ca), lipid rich necrotic core (LRNC), and fibrotic plaques (FP). Plaque vulnerability of these samples was assessed pathologically to serve as a bench mark to validate computational findings. The 3D ex vivo MRI data were read by a self-developed software package Atherosclerotic Plaque Imaging Analysis (APIA) written in MATLAB® (THE MATHWORKS, Natick, Mass.) and also validated by histological analysis.

All segmented 2D slices were read into an ADINA® input file (.in file). 3D plaque geometry was reconstructed following the procedure described in Tang et al. (Ann. Biomed. Eng., 32(7), pp. 947-960, 2004). As described above, FIGS. 5a-e show one slice selected from a 36-slice data set of a human coronary plaque sample and plaque component contour plots based on histological segmentation data. Individual contour plots, FIG. 5a-e, show that T1 weighting, FIG. 5a, is better for assessing the two Ca pools, T2 weighting, FIG. 5c, is better for assessing the lumen and outer boundary, and middle-T2 weighting, FIG. 5b, is better for assessing the lipid core.

The diameter of the vessel shown in FIGS. 5a-5e is about 5-6 mm. Some smoothing (third-order spline) was applied to correct numerical and MR artifacts, as well as overly unsmooth spots that affect the convergence of the model. Smoothing was kept to minimum only to remove data artifacts and extreme sharp angles which affect code convergence. Critical morphological features (such as plaque cap thickness) were carefully kept unchanged so that the accuracy of computational predictions will not be affected. The vessel was extended uniformly at both ends by 3 cm and 6 cm for the no-bending case, respectively, to avoid flow entrance and end effects. For cases with cyclic bending, the vessel was extended at both ends by 4 mm to keep vessel length reasonable for implementing cyclic bending conditions.

The Component-Fitting Mesh Generation Technique

Because plaques have complex irregular geometries with component inclusions which are challenging for mesh generation, a component-fitting mesh generation technique to generate mesh for 2D and 3D models was developed, as described above with reference to FIGS. 6A-6B and 7A-7B. The mesh generation technique includes interpolating a plurality of data points, such as data points collected using MRI, that correspond to a contour of the blood vessel, to yield an interpolated contour. Using this technique, the 3D plaque domain is divided into hundreds of small "volumes" to curve-fit the irregular plaque geometry with plaque component inclusions. The technique includes generating a structural model, representing 3D structural characteristics of the blood vessel, and a fluid model, representing 3D characteristics of fluid flow, based on respective interpolated contours. The technique further includes generating a vascular model, including a 3D FSI model, based on the structural and fluid models.

For the plaque sample given in FIGS. 5a-e, 3D surfaces, volumes, and computational mesh were made under the ADINA® computing environment. Corresponding meshes 830, 840 are shown in FIGS. 8c-d. The finite element ADINA® FSI solid model (of mesh 830) has 804 volumes, 59360 elements (8-nodes brick element), 64050 nodes. The fluid part (mesh 840) has 216 volumes, 71481 elements (4-nodes tetrahedral element), 14803 nodes. Mesh analysis was performed by decreasing mesh size by 10% (in each dimension) until solution differences were less than 2%. The mesh was then chosen for our simulations.

Figure 10A:
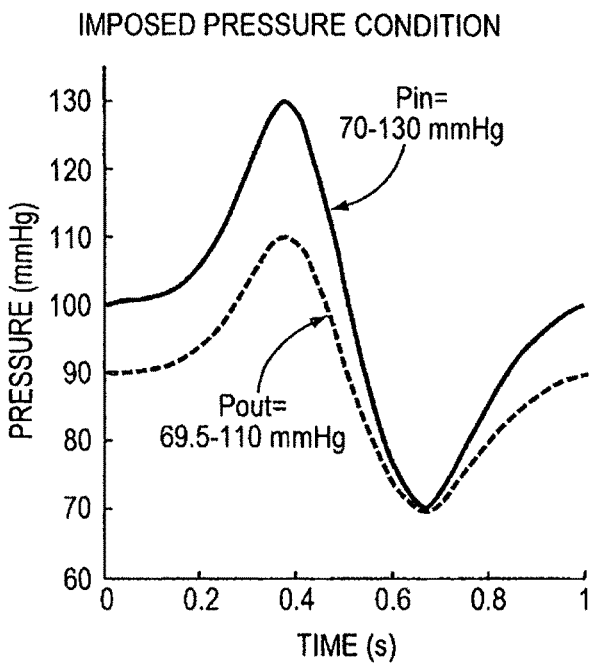
FIGS. 10a-10b show prescribed pressure conditions for the baseline model and corresponding flow rates. (a) A simplified pressure profile for a human artery was scaled to 70-130 mmHg and used as the upstream pressure (Pin). Downstream pressure was chosen so that flow rate was within physiological range; (b) Flow rate corresponding to the prescribed pressure conditions with and without cyclic bending. Cyclic bending reduced max flow rate by about 2.5%.

The Anisotropic and Isotropic Multi-Component FSI Models with Cyclic Bending 3D anisotropic and isotropic multi-component FSI models were introduced to evaluate the effects of cyclic bending and anisotropic properties on stress and strain distributions in coronary plaques using the plaque sample re-constructed as described above in the context of FIGS. 5a-e. Blood flow was assumed to be laminar, Newtonian, and incompressible. The Navier-Stokes equations with arbitrary Lagrangian Eulerian (ALE) formulation were used as the governing equations. Physiological pressure conditions were prescribed at both inlet and outlet (FIG. 10a). No-slip conditions and natural traction equilibrium conditions are assumed at all interfaces. Putting these together yields the following equations (summation convention is used):

$$\rho(\partial u/\partial t + ((u-u_g)\cdot\nabla)u) = -\nabla p + \mu\nabla^2 u, \quad (1)$$

$$\nabla\cdot u = 0, \quad (2)$$

$$u|_\Gamma = \partial x/\partial t, \partial u/\partial n|_{inlet,\ outlet} = 0, \quad (3)$$

$$p|_{inlet}=p_{in}(t), p|_{outlet}=p_{out}(t), \quad (4)$$

$$\rho v_{i,t}=\tau_{ij,j}, i,j=1,2,3; \text{sum over } j, \quad (5)$$

$$\epsilon_{ij}=(v_{i,j}+v_{j,i}+v_{\alpha,i}v_{\alpha,j})/2, i,j,\alpha=1,2,3 \quad (6)$$

$$\sigma_{ij}\cdot n_j|_{out\_wall}=0, \quad (7)$$

$$\sigma^r_{ij}\cdot n_j|_{interface}=\sigma^s_{ij}\cdot n_j|_{interface}, \quad (8)$$

where u and p are fluid velocity and pressure, $u_g$ is mesh velocity, $\mu$ is the dynamic viscosity, $\rho$ is density, $\Gamma$ stands for vessel inner boundary, $f_{\cdot,j}$ stands for derivative of f with respect to the jth variable, $\sigma$ is stress tensor (superscripts indicate different materials), $\epsilon$ is strain tensor, v is solid displacement vector. Superscript letters "r" and "s" were used to indicate different materials (fluid, different plaque components). For simplicity, all material densities were set to 1 in this formulation. Details of material models and other boundary conditions are further explained below.

To get the constitutive stress-strain relationship for the isotropic model, both artery vessel material and plaque components in the plaque were assumed to be hyperelastic, isotropic, incompressible and homogeneous. The 3D nonlinear modified Mooney-Rivlin (M-R) model was used to describe the material properties of the vessel wall and plaque components.

The strain energy function for M-R model is given by, $$W=c_1(I_1-3)+c_2(I_2-3)+D_1[\exp(D_2(I_1-3))-1], \quad (9)$$

$$I_1=\Sigma C_{ii}, I_2=\frac{1}{2}[I_1^2-c_{ij}C_{ij}], \quad (10)$$

where $I_1$ and $I_2$ are the first and second strain invariants, $C=[C_{ij}]=X^T X$ is the right Cauchy-Green deformation tensor, $X=[X_{ij}]=[\partial x_i/\partial a_j]$, $(x_i)$ is current position, $(a_i)$ is original position, $c_i$ and $D_i$ for i=1, 2 are material parameters chosen to match experimental measurements for fibrous tissue and data in the current literature for lipid pool and calcifications. 3D stress and strain relations can be obtained by finding various partial derivatives of the strain energy function with respect to proper variables (strain/stretch components). In particular, setting material density $\rho=1$ g·cm$^{-3}$ and assuming incompressibility, $$\lambda_1\lambda_2\lambda_3=1, \lambda_2=\lambda_3, \lambda=\lambda_1, \quad (11)$$

where $\lambda_1$, $\lambda_2$ and $\lambda_3$ are stretch ratios in the (x,y,z) directions respectively, the uniaxial stress/stretch relation for an isotropic material is obtained from Eq. (9), as follows:

$$\sigma=\partial W/\partial \lambda=c_1[2\lambda-2\lambda^{-2}]+c_2[2-2\lambda^{-3}]+D_1 D_2[2\lambda-2\lambda^{-2}]\exp[D_2(\lambda^2+2\lambda^{-1}-3)]. \quad (12)$$

Figure 11A:
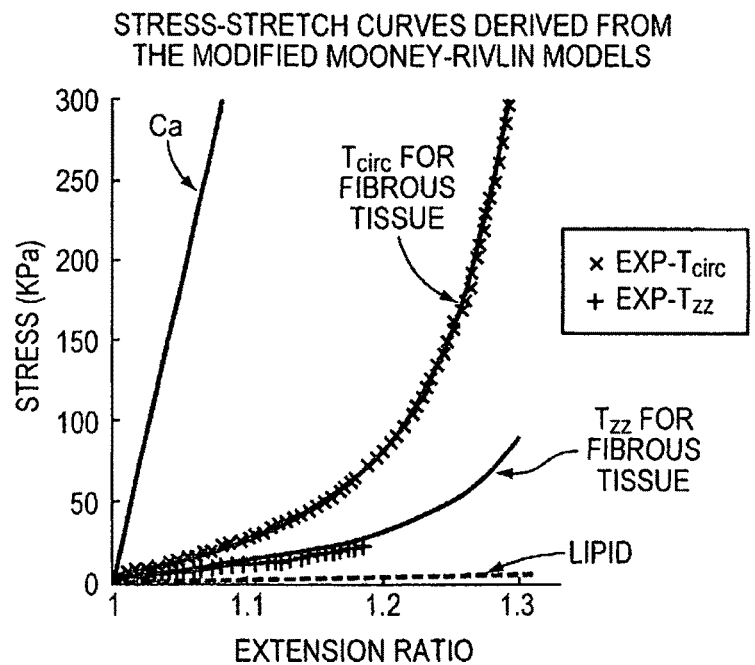
FIGS. 11a-11b show material stress-stretch curves and imposed curvature conditions. (a) Axial and circumferential stress-stretch data (marked by + and x, respectively) measured from a human coronary specimen and stress-stretch matching curves derived from the modified anisotropic Mooney-Rivlin models for fibrous tissue (vessel). Stress-stretch curves for lipid pool and calcification models were also included; (b) Imposed curvature conditions based on human coronary curvature variation data.
Figure 11B:
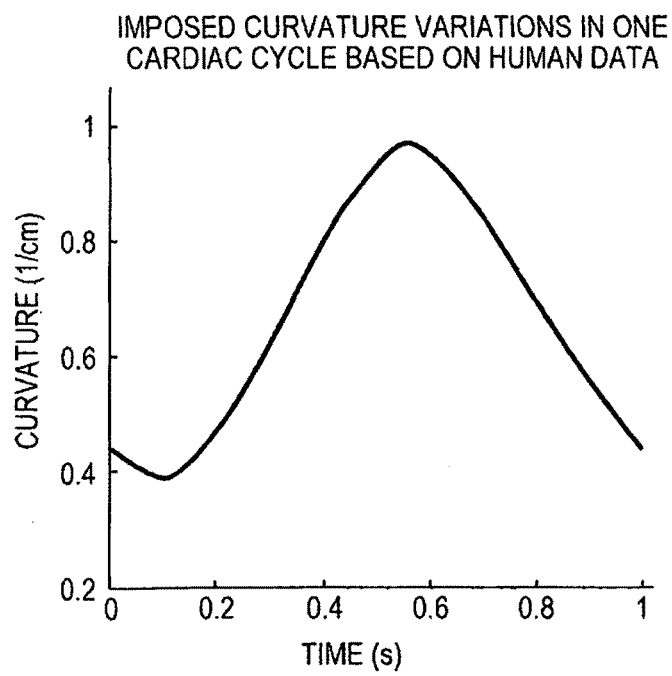
Figure 12A:
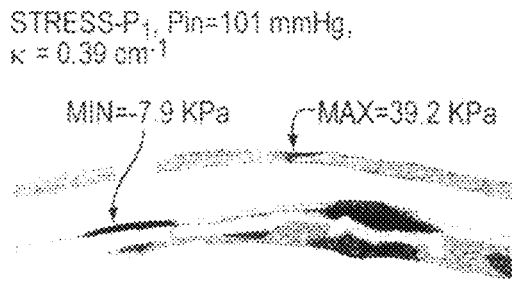
FIGS. 12a-12d show principal stress (Stress-$P_1$) and principal strain (Strain-$P_1$) distributions from a model (Model 1 with cyclic bending) corresponding to maximum and minimum curvature conditions.
Figure 12B:
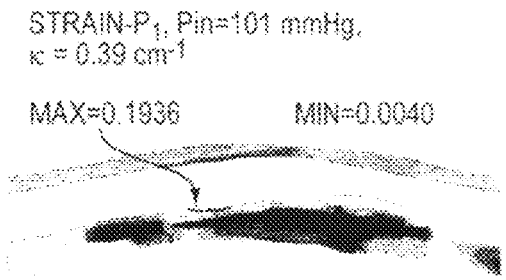
Figure 12C:
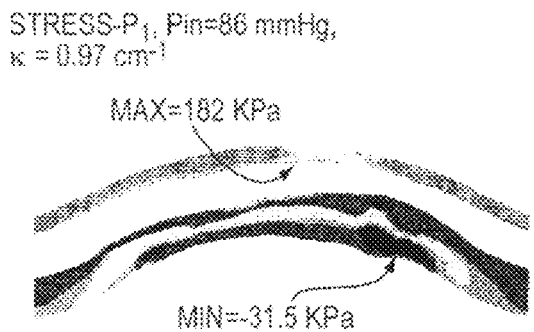
Figure 12D:
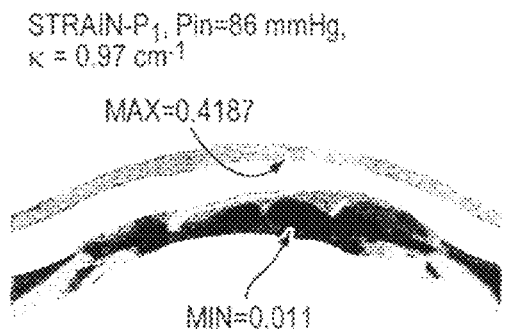
Figure 12E:
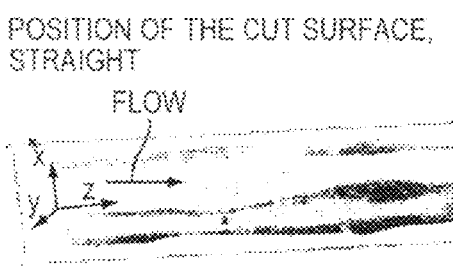
FIGS. 12e-f show the position of the cut-surface.
Figure 12F:
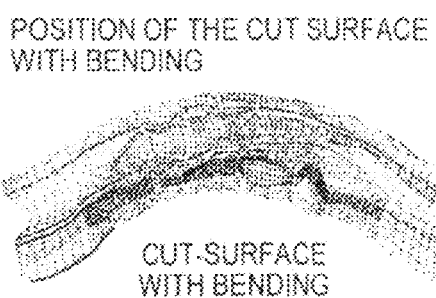
Figure 14A:
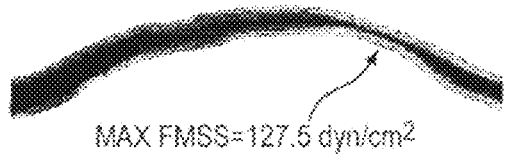
FIGS. 14a-14d are plots of flow maximum shear stress (FMSS) and velocity from Model 1 (with bending) and Model 2 (no bending). A comparison of the plots shows that cyclic bending has modest effects (<15%) on flow velocity and maximum shear stress.
Figure 14B:
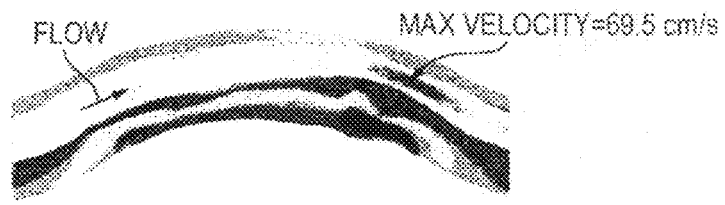
Figure 14C:
Figure 14D:
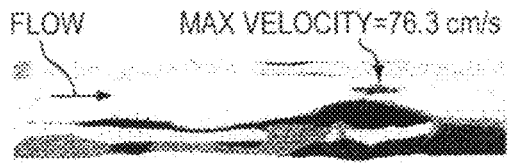

Using the modified Mooney-Rivlin model available in ADINA® and adding an additional anisotropic term to Eq. (9), the anisotropic (transversely isotropic) strain energy density function for the anisotropic FSI model is obtained:

$$W = c_1(I_1-3)+D_1[\exp(D_2(I_1-3))-1]+\frac{K_1}{2K_2}[\exp[K_2(I_4-1)^2]-1], \quad (13)$$

where $I_4=C_{ij}(n_c)_i(n_c)_j$, $C_{ij}$ is the Cauchy-Green deformation tensor, $n_c$ is the circumferential direction of the vessel, $K_1$ and $K_2$ are material constants. A two-step least-squares method was used to determine the parameter values in Eq. (13) to fit the experimental circumferential and axial stress-stretch data. Step 1. By choosing the principal axes as local coordinate axes, calculations are simplified. Noticing that $\lambda_r\lambda_c\lambda_z=1$, $\lambda_r=\lambda_z$ (there are radial and axial directions, respectively), $\sigma=J^{-1}FTF^T$ where $\sigma$ is Cauchy stress, T is the second Piola-Kirchhoff stress, and $T_{cc}=\partial W/\partial E_{cc}, T_{zz}=\partial W/\partial E_{zz}$, one obtains from Eq. (13):

$$\sigma_z = 2c_z\left(1-\frac{1}{c_z^2 c_c}\right)C_1 + 2c_z\left(1-\frac{1}{c_z^2 c_c}\right)D_1 D_2 e^{D_2(I_1-3)} \quad (14)$$
$$\equiv A_1 C_1 + A_2 D_1,$$

where $c_z=(C)_{zz}=(F^T F)_{zz}$, $c_c=(F^T F)_{cc}$ are components of the right Cauchy-Green deformation tensor. Using stress-stretch values obtained from measurements (FIG. 11) and with $D_2$ and $K_2$ fixed, a least square approximation technique was used to obtain $C_1$, $D_1$, $K_1$ (all functions of $D_2, K_2$).
Step 2. Let $D_2$ and $K_2$ change from −100 to 100, Step 1 was performed for all ($D_2$, $K_2$) combinations with initial increment equal to 10 to get the corresponding $C_1$, $D_1$, $K_1$ values and the least squares fitting errors. Optimal ($D_2$, $K_2$) and the associated $C_1$, $D_1$, $K_1$ values are determined by choosing the pair corresponding to a minimum fitting error. The searching increment for ($D_2$, $K_2$) started at 10 for [−100,100] and was then refined to 1, and 0.1 when the search domain was reduced. FIG. 11a shows that the model with parameters selected with this procedure fits very well with the measured experimental data. Parameter values numerically determined from this optimization process are: anisotropic model for fibrous tissue: $C_1$=8.2917 KPa, $D_1$=0.9072 KPa, $D_2$=3.1, $K_1$=8.8240 KPa, $K_2$=3.7000; corresponding isotropic models: circumferential (used for isotropic fibrous tissue): $C_1$=28.1443 KPa, $D_1$=1.3101 KPa, $D_2$=11.5; axial: $C_1$=14.0722 KPa, $D_1$=0.6551 KPa, $D_2$=9.2. These measurements are consistent with data available in the literature.

Isotropic models were used for calcification (Ca) and necrotic lipid-rich core. Because calcification is much stiffer than fibrous tissue, and lipid core is much softer than fibrous tissue, the following parameter values were used: Ca, $C_1$=281.443 KPa, $D_1$=13.101 KPa ($C_1$ and $D_1$ are 10 times of the corresponding values for normal tissue), $D_2$=11.5; lipid pool: $C_1$=0.5 KPa, $D_1$=0.5 KPa, D2=0.5 (these small numbers were chosen so that lipid would be very soft).

Cyclic arterial bending secondary to cardiac motion was introduced into the computational model by specifying a cyclic nonuniform 3D displacement function d(x,y,z,t) on the lower edge of the outer surface of the vessel. The displacement function could be adjusted to achieve desirable curvature changes. The imposed curvature variation is given in FIG. 11b using human left anterior descending (LAD) coronary curvature variation data. The displacement function was set to zero at the two ends of the vessel together with some additional neighboring nodes so that a small portion of the vessel inlet/outlet was fixed when the vessel was bent. This should be taken into consideration when interpreting computational results from the near-end portion of the vessel. Additional length (4 mm at each end) was added to the vessel to avoid this computational artifact.

Solution Method.

The coupled FSI models were solved by a commercial finite-element package, such as ADINA® (ADINA R & D, Inc., Watertown, Mass., USA). ADINA® uses unstructured finite element methods for both fluid and solid models. Nonlinear incremental iterative procedures were used to handle fluid-structure interactions. Proper mesh was chosen to fit the shape of each component, the vessel, and the fluid domain. Finer mesh was used for thin plaque cap and components with sharp angles to get better resolution and handle high stress concentration behaviors. The governing finite element equations for both the solid and fluid models were solved by the Newton-Raphson iteration method.

Results

Computational simulations were conducted using the coronary plaque sample to quantify effects of anisotropic properties, cyclic bending and their combined effects with pressure (phase angle shift), plaque components, and axial stretch on flow and stress and strain distributions. Six models were used in the simulation: Model 1, baseline anisotropic model with plaque components, cyclic bending and pulsating pressure as prescribed in Section 2; Model 2, same as Model 1, but no bending; Model 3, same as Model 1, but no plaque components, i.e., the same material properties were assigned to Ca and lipid core components; Model 4 is the same as Model 1, but with no phase angle between cyclic bending and pressure, i.e., maximum pressure occurs with maximum bending; Model 5 has 10% axial pre-stretch added to Model 1; Model 6, same as Model 1, but isotropic model (matching circumferential stress-stretch curve) was used for the normal tissue. Because of that, it should be noted that vessel material in Model 6 is much stiffer than that in Model 1. For Model 5, the vessel was stretched (10% axial stretch) and pressurized first, then the inlet and outlet were fixed and cyclic bending was applied.

Cyclic Bending Leads to Considerable Stress and Strain Variations in the Plaque.

FIGS. 12 and 13 show maximum principal stress (Stress-$P_1$) and maximum principal strain (Strain-$P_1$) plots from Model 1 (with cyclic bending) and Model 2 (without cyclic bending), corresponding to maximum ($\kappa=0.97$ cm$^{-1}$) and minimum ($\kappa=0.39$ cm$^{-1}$) curvature conditions in one cardiac cycle. For Model 1, maximum Stress-$P_1$ from FIG. 12c (maximum curvature) was 360% higher than that from FIG. 12a (minimum curvature) even though pressure was lower in FIG. 12c. Maximum Stress-$P_1$ value from FIG. 12c (the bending case) was also 340% higher than that from the no-bending case (FIG. 13c). Maximum Strain-$P_1$ value from FIG. 12d (the bending case) was also 134% higher than that from the no-bending case (FIG. 13d). FIG. 13 shows that stress and strain variations are dominated by pressure changes when no cyclic bending is imposed. Strain distributions in the plaque showed similar behaviors. These results show very clearly that cyclic bending leads to large stress and strain increases (100-360%) in the plaque and must be included in computational models for coronary plaques for accurate stress and strain predictions. Two significant figures were used in percentage calculations.

Cyclic Bending Caused Only Modest Flow Velocity and Shear Stress Changes.

Figure 10B:
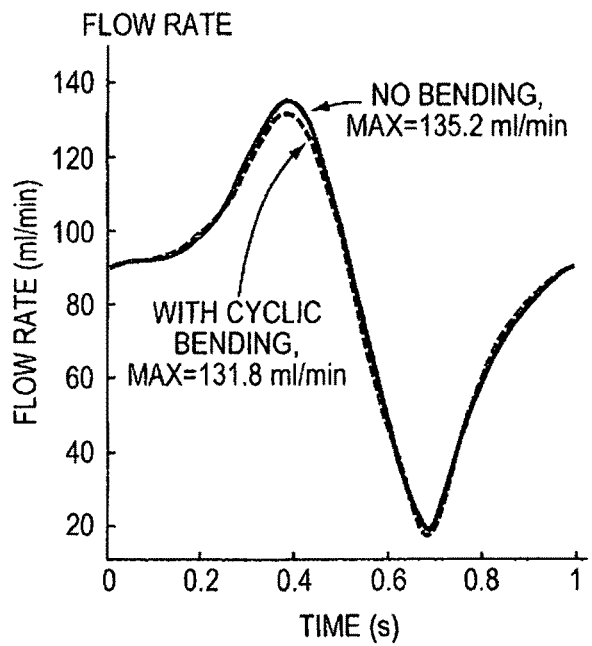

Effects of cyclic bending on flow behaviors are more modest because flow is more closely related to pressure drop across the plaque segment which was kept the same for both bending and no-bending models. Cyclic bending does increase flow resistant because of the increased curvature ($\kappa=0.97$ cm$^{-1}$) of the bending case. FIG. 14 compares flow maximum shear stress (FMSS) and velocity for the bending and no-bending cases corresponding to the time step with maximum curvature. Table 1 lists the maximum FMSS and velocity values for three curvature conditions. Maximum velocity from Model 1 corresponding to maximum curvature was 69.5 cm/s, which increased to 76.3 cm/s for the no-bending case, a 9.8% increase. FMSS actually decreased from 127.5 dyn/cm$^2$ for the bending case to 108.4 dyn/cm$^2$ (15%) for the non-bending case. It should be noted that computational maximum values were observed at only one or a few computational nodal points, while experimental data measured by medical devices are often averaged values of the selected region of interest (ROI). A second effect of bending may be seen in the overall flow rate during the cardiac cycle (see FIG. 10b). Maximum flow rates were 131.8 ml/min with bending, and 135.2 ml/min (2.5% increase) without bending, respectively, likely due to additional viscous losses associated with the changing curvatures.

TABLE 1

Comparison of maximum flow maximum shear stress (FMSS) and velocity values from Model 1 (with bending) and Model 2 (no bending) shows that cyclic bending has modest effects (<15%) on flow velocity and maximum shear stress.

| Cases | Max Velocity | Max FMSS | Max Velocity | Max FMSS | Max Velocity | Max FMSS |
|---|---|---|---|---|---|---|
| Model 1 Baseline | $\kappa = 0.39$ 1/cm, Pin = 101 | | $\kappa = 0.78$ 1/cm, Pin = 130 | | $\kappa = 0.97$ 1/cm, Pin = 86 | |
| | 98.7 | 147.5 | 133.6 | 236.1 | 69.5 | 127.5 |
| Model 2 No Bending | $\kappa = 0$, Pin = 101 | | $\kappa = 0$, Pin = 130 | | $\kappa = 0$, Pin = 86 | |
| | 99.1 | 140.9 | 135.1 | 195.7 | 76.3 | 108.4 |

Combined Effects of Bending with Plaque Components, Phase Angle, and Axial Stretch.

Figure 15A:
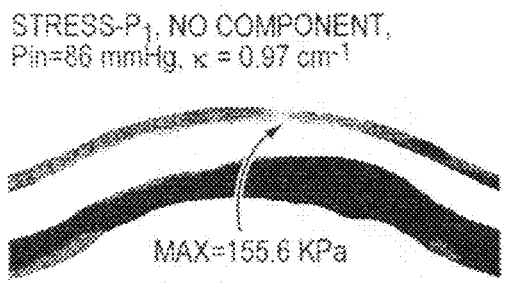
FIGS. 15a-15f illustrate the combined effects of plaque components, pressure/curvature phase angle, and axial stretch with cyclic bending on stress and strain distributions.
Figure 15B:
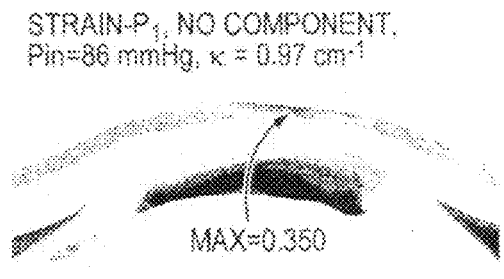
Figure 15C:
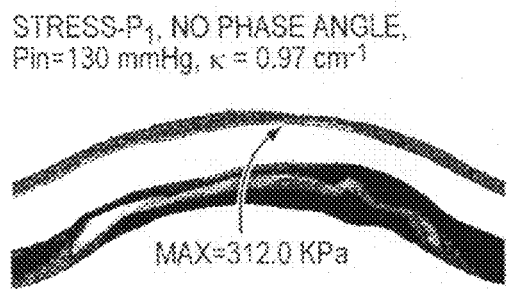
Figure 15D:
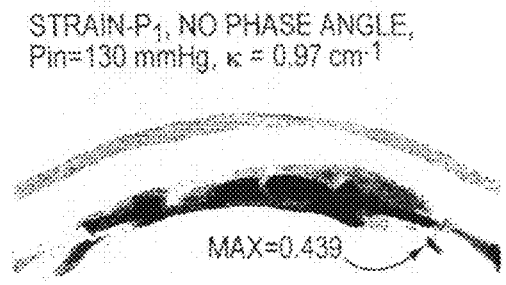
Figure 15E:
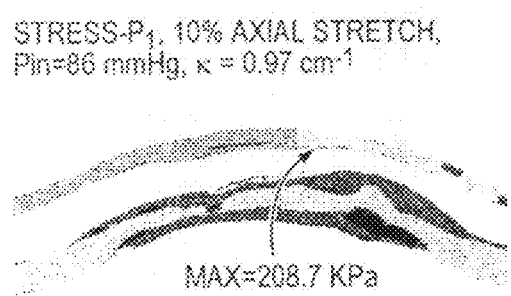
Figure 15F:
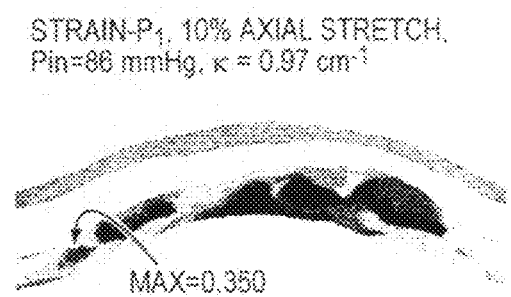

Major contributing factors for stress-strain distributions in a plaque include plaque morphology, plaque structure with components, pressure condition, material properties, and axial stretch. FIG. 15 gives Stress-$P_1$ and Strain-$P_1$ plots from Model 3 (no plaque components), Model 4 (no phase angle) and Model 5 (with 10% axial stretch) to show the patterns of stress and strain distributions. Table 2 lists the maximum Stress-$P_1$ and Strain-$P_1$ from Models 1-5 corresponding to maximum and minimum curvature and pressure conditions. Maximum Stress-$P_1$ and Strain-$P_1$ from Model 1 at minimum curvature were used as the base numbers for comparison purpose. Overall, cyclic bending led to 300%-800% higher maximum stress values and 80%485% higher maximum strain values. Models without plaque components led to slightly less stress and strain variations because stress and strain distributions were more uniform (FIG. 15a-b). When maximum pressure and maximum bending occurred simultaneously ($\alpha=0$, $\alpha$ is the phase angle between maximum curvature and maximum pressure), maximum stress value was 696% higher than the base stress value. With a 10% axial stretch added to Model 1, maximum Stress-$P_1$ value for $\kappa=0.39$ 1/cm, Pin=101 mmHg increased to 133.4 KPa, a 240% increase from that of Model 1. However, effects of each contributing factor on stress and strain distributions were of localized nature, and were not uniform for the cardiac cycle. Localized stress and strain behaviors will be tracked at selected sites and results will be presented below.

TABLE 2

Summary of maximum Stress-$P_1$ and Strain-$P_1$ values from five models showing that cyclic bending has large effects on stress and strain values in coronary plaques.

| Cases | Max Stress-$P_1$ (KPa) | Max Strain-$P_1$ | Max Stress-$P_1$ (KPa) | Max Strain-$P_1$ |
|---|---|---|---|---|
| | $\kappa = 0.39$ l/cm, Pin = 101 | | $\kappa = 0.97$ l/cm, Pin = 86 | |
| Model 1 | 39.2 (100%) | 0.194 (100%) | 182 (464%) | 0.419 (216%) |
| Model 2 | 46.8 (119%) | 0.201 (104%) | 41.5 (106%) | 0.179 (92.2%) |
| Model 3 | 38.1 (97.1%) | 0.187 (96.4%) | 155.6 (397%) | 0.350 (180%) |
| Model 5 | 133.4 (340%) | 0.372 (192%) | 208.7 (532%) | 0.553 (285%) |
| Model 4 | $\kappa = 0.39$ l/cm, Pin = 96.4 | | $\kappa = 0.97$ l/cm, Pin = 130 | |
| | 37.4 (95.4%) | 0.185 (95.3%) | 312.0 (796%) | 0.439 (226%) |

Comparison of Anisotropic and Isotropic Models

Figure 16A:
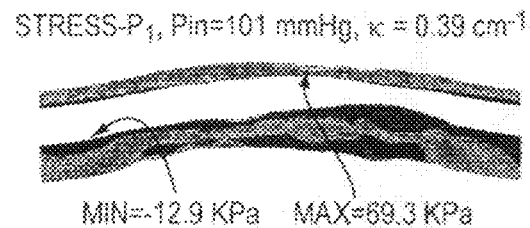
FIGS. 16a-16d are Stress-$P_1$ and Strain-$P_1$ plots from the isotropic model (Model 6) with cyclic bending showing different stress and strain distribution patterns.
Figure 16B:
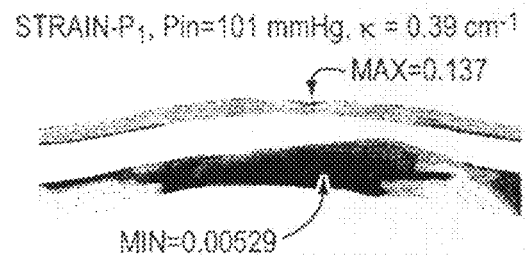
Figure 16C:
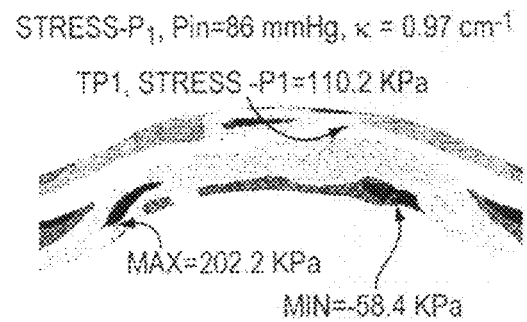
Figure 16D:

The measured circumferential stress-stretch data from the human coronary specimen was used to construct an isotropic model with cyclic bending to quantify the differences between the anisotropic and isotropic models. It should be noted that the normal tissue in the isotropic model is stiffer compared to that in the anisotropic model because circumferential stress-stretch data was used. FIG. 16 presents Stress-$P_1$ and Strain-$P_1$ plots from Model 6 (isotropic with cyclic bending) corresponding to maximum and minimum curvature conditions. Strain values from Model 6 are noticeably lower because the material used is stiffer. Location of maximum Stress-$P_1$ is different for the maximum curvature case (FIG. 16c). Using the same location at Tracking Point 1 (TP1), Stress-$P_1$ value (110.2 KPa) from Model 6 is 65% lower than that from Model 1 (182 KPa). Stress differences caused by the calcification block is more noticeable in FIG. 12c than that in FIG. 16c because of the stiffer normal tissue material in Model 6.

Local Stress and Strain Behaviors Tracked at Selected Critical Sites

Figure 17A:
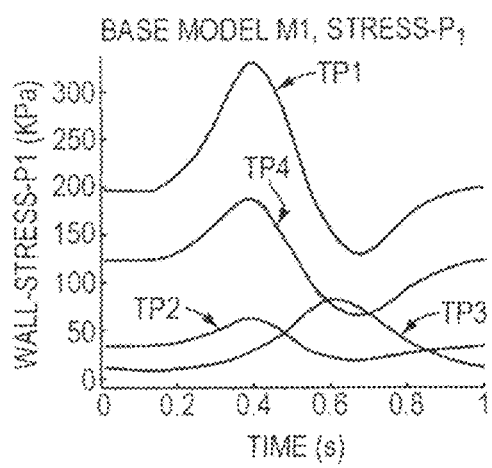
FIGS. 17a-17d are plots of local Stress-$P_1$ variations tracked at four selected locations from four models showing cyclic bending causes large stress variations in the coronary plaque.
Figure 17B:
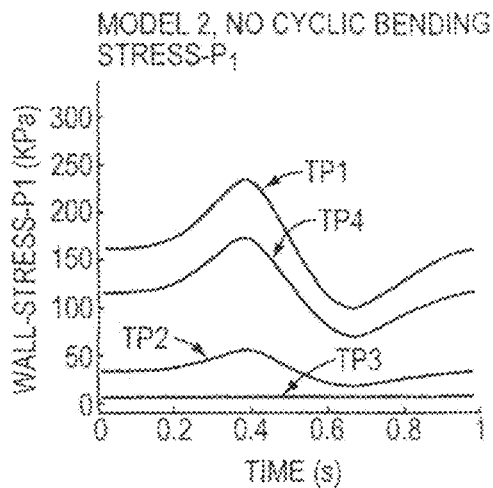
Figure 17C:
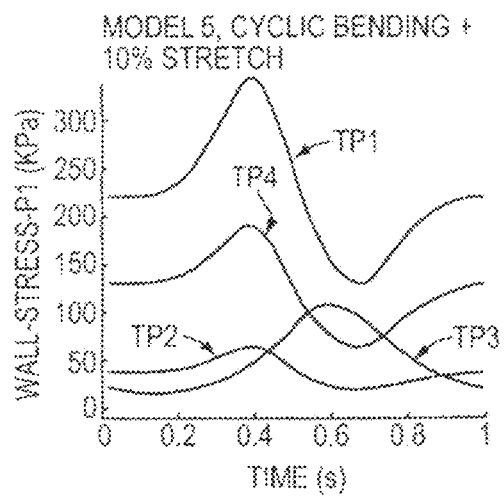
Figure 17D:
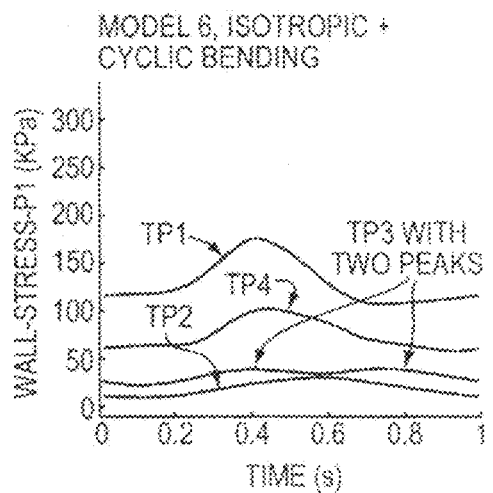
Figure 17E:
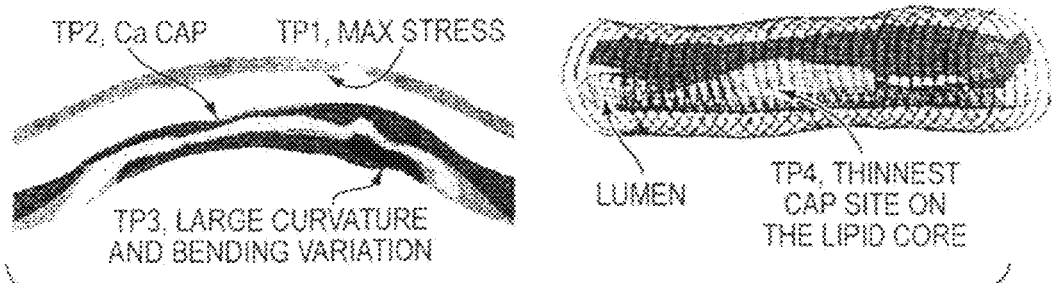
FIG. 17e illustrates the location of tracking points TP1-TP4 of FIGS. 17a-17d. TP1: a location where global maximum Stress-$P_s$ was found; TP2: calcification plaque cap (thinnest site); TP3; a location on the bending side with a large local curvature; TP4: lipid core plaque cap.

With so many factors involved, it is hard to compare the differences of 4D (time+3D space) stress and strain distributions from different models. It has also been reported that plaque vulnerability may be more closely associated with local stress and strain behaviors than with global maximum stress and strain values. With this in mind, FIG. 17 shows Stress-$P_1$ variations from 4 models tracked at four selected sites. Track Point 1 (TP1) is the location where global maximum Stress-$P_1$ was found under maximum curvature for Models 1 and 3-5. Track Point 2 (TP2) is located at the plaque cap (thinnest site) over the calcification block. Track Point 3 (TP3) is at a location where the plaque has a large local curvature. Track Point 4 (TP4) is located at the plaque cap (thinnest site) over the lipid core. FIG. 17e shows the location of all four tracking points. Maximum and minimum values of all tracking curves from the 6 models are summarized in Table 3. Several observations can be made from the curves in FIG. 17a-d) Effects of cyclic bending and pulsating pressure depends heavily on the location of the tracking sites. TP1, TP2 and TP4 are on lumen surface and Stress-$P_1$ was affected most by the pulsating pressure. TP3 is located at the outer surface of the vessel which is affected the least by pressure. Being on the bending side, Stress-$P_1$ is affected the most by cyclic bending, reaching its maximum at maximum bending. Overall, effect of cyclic bending is the strongest on the bending side (the lower edge of the vessel), and becomes weaker as the location moves further away from the bending side. Effect of pulsating pressure becomes less as we move towards the outer surface of the vessel; b) Stress-$P_1$ variations are greater at the cap on the lipid core than that on the cap on the calcification block; c) Peak Stress-$P_1$ values from Model 1 at TP1, TP2 and TP4 are 44.5%, 21.6, 11.2% higher than those from Model 2. More noticeably, peak Stress-$P_1$ value (80.3 KPa) at TP3 is 26.7 times higher than that from the near-zero stress values (peak value=2.90 KPa) from Model 2; d) In general, Stress-$P_1$ values from the anisotropic models tracked at TP1-TP4 were about 80%-100% higher than those from the isotropic model (Model 6). The peaking time showed some delay at TP1, TP2 and TP4. TP3 curve has two peaks, indicating that the bending and pressure effects were at a balancing point. Table 3 offers maximum and minimum values for the 4 tracking points from 6 models.

TABLE 3

Summary of maximum and minimum Stress-$P_1$ and Strain-$P_1$ values in one cardiac cycle at four tracking sites from six models showing that cyclic bending and anisotropic properties have large effects on critical stress and strain values in coronary plaques.

| Model | TP1 Max Stress-$P_1$ (KPa) | TP2 Max Stress-$P_1$ (KPa) | TP3 Max Stress-$P_1$ (KPa) | TP4 Max Stress-$P_1$ (KPa) | TP1 Max Strain-$P_1$ | TP2 Max Strain-$P_1$ | TP3 Max Strain-$P_1$ | TP4 Max Strain-$P_1$ |
|---|---|---|---|---|---|---|---|---|
| Model 1 | 329.9 | 61.4 | 80.3 | 187.9 | 0.5019 | 0.2446 | 0.3955 | 0.3382 |
| Model 2 | 228.3 | 50.5 | 2.89 | 167.4 | 0.5251 | 0.2318 | 0.0420 | 0.3329 |
| Model 3 | 309.7 | 51.8 | 22.41 | 136.8 | 0.4719 | 0.2184 | 0.1857 | 0.3188 |
| Model 4 | 343.5 | 61.5 | 66.67 | 183.2 | 0.4942 | 0.2449 | 0.3816 | 0.3352 |
| Model 5 | 344.7 | 64.2 | 108.3 | 191.1 | 0.4933 | 0.2481 | 0.4168 | 0.3423 |
| Model 6 | 176.3 | 30.2 | 39.72 | 102.0 | 0.2231 | 0.1063 | 0.1268 | 0.2025 |

TABLE 3-continued

Summary of maximum and minimum Stress-$P_1$ and Strain-$P_1$ values in one cardiac cycle at four tracking sites from six models showing that cyclic bending and anisotropic properties have large effects on critical stress and strain values in coronary plaques.

| Model | TP1 Min Stress-$P_1$ (KPa) | TP2 Min Stress-$P_1$ (KPa) | TP3 Min Stress-$P_1$ (KPa) | TP4 Min Stress-$P_1$ (KPa) | TP1 Min Strain-$P_1$ | TP2 Min Strain-$P_1$ | TP3 Min Strain-$P_1$ | TP4 Min Strain-$P_1$ |
|---|---|---|---|---|---|---|---|---|
| Model 1 | 128.4 | 16.86 | 7.56 | 64.16 | 0.3786 | 0.1318 | 0.1012 | 0.2387 |
| Model 2 | 93.3 | 13.63 | 1.63 | 64.89 | 0.3937 | 0.1228 | 0.0192 | 0.2460 |
| Model 3 | 126.3 | 13.32 | 6.14 | 41.52 | 0.3604 | 0.1063 | 0.0627 | 0.2070 |
| Model 4 | 123.4 | 16.80 | 7.82 | 67.76 | 0.3851 | 0.1041 | 0.1041 | 0.2431 |
| Model 5 | 129.8 | 18.90 | 15.23 | 64.67 | 0.3722 | 0.1623 | 0.1063 | 0.2723 |
| Model 6 | 107.8 | 9.41 | 22.18 | 57.70 | 0.1670 | 0.0479 | 0.0935 | 0.1049 |

These results indicate that cyclic bending, anisotropic properties, pressure, plaque components, and axial stretch are major contributing factors to stress conditions in coronary plaques. Their effects on stress distributions can be in the order of 50%-800% depending on location and contributing factors. Combined effects may lead to complex stress and strain behavior changes. The localized tracking technique described above may be the right approach to reveal critical stress and strain information at rupture-prone sites for better plaque assessment.

Critical Site Tracking (CST) Method to Study Complex Flow, and Stress and Strain Behaviors.

It can be seen clearly that 3D flow and 3D stress and strain behaviors in the plaque are very complex. It is hard to quantify the effect of the contributing factors (including cyclic bending, anisotropic material properties, pulsating pressure, plaque structure, and axial stretch) in the time-dependent full 3D setting, especially when several factors are combined at the same time. A critical site tracking (CST) technique reduces the full 3D investigation to site-tracking at selected locations and helps to identify the useful and relevant information much more clearly with less effort. The results presented above demonstrate the effectiveness of the CST technique. It has been shown that plaque vulnerability may correlate more closely with stress/strain values at certain critical sites which are prone to rupture. This suggests that the CST technique can be used in atherosclerotic plaque assessment and other investigations where localized information are critical to the problem being investigated.

In an embodiment of the invention, critical mechanical analysis (964) includes CST. The computer-implemented method for automatically generating a vascular model of a blood vessel of the invention includes generating a vascular model based on the generated 3D structural and fluid models. Advantageously, the vascular model includes 3D fluid-structure interactions (FSIs) in the blood vessel. In addition, the method may include performing a mechanical analysis of the automatically generated vascular model, such as an analysis of stress/strain distributions obtained from the mathematical FSI model, to identify factors associated with the vessel. Critical site selection and tracking combined with stress/strain data at those sites may be used to identify a mechanical factor, such as a quantitative index corresponding to a disease state of the vessel.

Benchmark Model for Coronary Plaques: Major Contributing Factors to Plaque Stress and Strain Distributions.

It is of vital importance to choose a coronary plaque model with proper model assumptions and initial and boundary conditions so that accurate flow and stress and strain information can be obtained for rupture risk assessment. The model should be as simple as possible so that cost and effort can be minimized, yet "complete" enough to include all major factors contributing to the problem (plaque mechanical analysis and vulnerability assessment) under investigation. It was previously demonstrated that blood pressure, material properties, plaque structure and components, fluid-structure interactions, initial pressurization and axial stretch are important and should be included in plaque models. As described above, anisotropic vessel properties and cyclic bending are added into the "major factor" list. The above results indicate that each of the five major factors (pulsating pressure, cyclic bending, material properties, plaque structure, and axial stretch) may affect critical stress and strain conditions from 50% to 800% or even more. It should be understood that results presented above were from one plaque sample. Embodiments of the present invention can be used to conduct more patient studies (including healthy volunteers) to generate a database for benchmark ranges of biological parameters and critical flow and stress and strain values. For example, the order of importance of high blood pressure, plaque components and structure, cyclic bending, material properties, and axial stretch may be evaluated using more plaque samples with a wide range of combinations of various components, especially large lipid pools and thin caps.

Embodiments of the current invention may include turbulence, lumen surface weakening and inflammation, vessel viscoelastic properties, and non-Newtonian flow properties. Turbulence may be present for severe stenosis. Lumen surface condition are important for plaque vulnerability analysis and can be included in an embodiment by adjusting the stiffness of the area affected. It is known that vessel viscoelastic properties and non-Newtonian flow properties have very limited effects (<5%) on flow, stress, and strain values and may be omitted for computational cost saving (see Yang, C., et al., *In Vivo/Ex Vivo MRI-Based 3D Models with Fluid-Structure Interactions for Human Atherosclerotic Plaques Compared with Fluid/Wall-Only Models*, CMES: Comput. Model. Eng. Sci. 19(3):233-245 (2007); and, Tang, D., et al., *A Viscoelastic Model and Meshless GFD Method for Blood Flow in Collapsible Stenotic Arteries*," Advances in Computational Engineering & Sciences, Chap. 11, International Conference on Computational Engineering and Sciences, Norcross, Ga., Tech Science Press (2002)).

Adding Cyclic Bending to Coronary Plaque Models with More Realistic Heart Motion.

The above results demonstrated that adding cyclic bending to coronary plaque models changes stress predictions up to 100% or more, which makes cyclic bending a necessary modeling addition for obtaining accurate stress-strain predictions and stress-based vulnerability assessment. In an embodiment of the present invention, cyclic bending was added by imposing a cyclic displacement at the lower edge of the vessel. The vessel may also be combined with a heart model or placed on a sphere so that the bending and stretching can be more realistic. An atherosclerotic artery, which may be rigidified by fibrotic and calcified components, may exhibit smaller amplitude of curvature variations, which may be implemented in an embodiment of the invention.

While this invention has been particularly shown and described with references to preferred embodiments thereof, it will be understood by those skilled in the art that various changes in form and details may be made therein without departing from the scope of the invention encompassed by the appended claims.

For example, the present invention may be implemented in a variety of computer architectures. The computer of FIG. 3 is for purposes of illustration and not a limitation of the present invention.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

What is claimed is:

1. A computer-implemented method of automatically generating a vascular model of a blood vessel, the method comprising:
    by a computer-based modeler executing on a processor and coupled to receive data from a data source,
       automatically interpolating a plurality of data points from the data source, the data points corresponding to a contour of a segmented image of the blood vessel, to yield an interpolated contour, the interpolation including circumferential interpolation and axial interpolation, the circumferential interpolation being performed in a two-dimensional slice representation of the blood vessel to correct for irregular shapes caused by image and segmentation distortion, the axial interpolation being performed along the blood vessel to generate another two-dimensional slice representation of the blood vessel to avoid sudden geometric changes due to angiography gaps;
       automatically generating a structural model, the structural model representing three-dimensional structural characteristics of the blood vessel, based on respective interpolated contours from the two-dimensional slice representations;
       automatically generating a fluid model, the fluid model representing three-dimensional characteristics of fluid flow within the vessel, based on respective interpolated contours from the two-dimensional slice representations; and
       automatically generating a vascular model based on the structural model and the fluid model, such that the processor outputs the vascular model.

2. The method of claim 1, performed for identification of mechanical factors corresponding to the blood vessel.

3. The method of claim 1, further including collecting the plurality of data points according to an imaging technique.

4. The method of claim 3, wherein the imaging technique is magnetic resonance imaging (MRI).

5. The method of claim 3, wherein the imaging technique is ultrasound.

6. The method of claim 5, wherein ultrasound is intravascular ultrasound.

7. The method of claim 1, further including performing a mechanical analysis of the vascular model to identify a factor associated with the vessel.

8. The method of claim 7, wherein the factor relates to a plaque in the vessel.

9. The method of claim 8, wherein the factor further relates to a potential rupture condition of the plaque.

10. The method of claim 7, wherein the mechanical analysis includes an analysis of a stress and strain distribution.

11. The method of claim 10, wherein the stress and strain distribution is modeled under an unsteady condition.

12. The method of claim 11, wherein the unsteady condition includes cyclic bending of the blood vessel.

13. The method of claim 1, wherein the vascular model includes three dimensional fluid-structure interactions (FSI) in the blood vessel.

14. The method of claim 13, wherein the vascular model includes any combination of isotropic models, anisotropic models, and multi-component models of the vessel.

15. The method of claim 1, wherein the blood vessel is an artery.

16. The method of claim 15, wherein the artery is a coronary artery.

17. The method of claim 15, wherein the artery is a carotid artery.

18. A computer system comprising:
    a data source containing a plurality of data points corresponding to a contour of a segmented image of a blood vessel; and
    a modeler executing on a processor and coupled to receive data from the data source, the modeler automatically interpolating the plurality of data points to yield an interpolated contour, the interpolation including circumferential interpolation and axial interpolation, the circumferential interpolation being performed in a two-dimensional slice representation of the blood vessel to correct for irregular shapes caused by image and segmentation distortion, the axial interpolation being performed along the blood vessel to generate another two-dimensional slice representation of the blood vessel to avoid sudden geometric changes due to angiography gaps, the modeler further automatically generating a structural model, a fluid model, and a vascular model based on the structural model and the fluid model, such that the processor outputs the vascular model, the structural model representing three-dimensional structural characteristics of the blood vessel, based on respective interpolated contours from the two-dimensional slice representations, the fluid model representing three-dimensional characteristics of fluid flow within the vessel, based on respective interpolated contours from the two-dimensional slice representations.

19. The computer system of clam 18, wherein the generation of the vascular model is performed for identification of mechanical factors corresponding to the blood vessel.

20. The computer system of claim 18, wherein the plurality of data points are data points collected according to an imaging technique.

21. The computer system of claim 20, wherein the imaging technique is magnetic resonance imaging (MRI).

22. The computer system of claim 20, wherein the imaging technique is ultrasound.

23. The computer system of claim 22, wherein ultrasound is intravascular ultrasound.

24. The computer system of claim 18, further including a routine for performing a mechanical analysis of the vascular model to identify a factor associated with the vessel.

25. The computer system of claim 24, wherein the factor relates to a plaque in the vessel.

26. The computer system of claim 25, wherein the factor further relates to a potential rupture condition of the plaque.

27. The computer system of claim 18, wherein the vascular model includes three dimensional fluid-structure interactions (FSI) in the blood vessel.

28. The computer system of claim 18, wherein the blood vessel is an artery.

29. The computer system of claim 28, wherein the artery is a coronary artery.

30. The computer system of claim 28, wherein the artery is a carotid artery.

* * * * *